United States Patent
Koshino

(10) Patent No.: US 12,138,124 B2
(45) Date of Patent: Nov. 12, 2024

(54) ULTRASOUND DIAGNOSTIC APPARATUS AND CONTROL METHOD OF ULTRASOUND DIAGNOSTIC APPARATUS

(71) Applicant: FUJIFILM Corporation, Tokyo (JP)

(72) Inventor: Riko Koshino, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/188,334

(22) Filed: Mar. 22, 2023

(65) Prior Publication Data

US 2023/0225708 A1 Jul. 20, 2023

Related U.S. Application Data

(63) Continuation of application No. PCT/JP2021/028029, filed on Jul. 29, 2021.

(30) Foreign Application Priority Data

Sep. 28, 2020 (JP) .................................. 2020-162405

(51) Int. Cl.
*A61B 8/00* (2006.01)
*A61B 8/08* (2006.01)
*G01S 7/52* (2006.01)

(52) U.S. Cl.
CPC ............ *A61B 8/463* (2013.01); *A61B 8/0825* (2013.01); *A61B 8/5261* (2013.01); *A61B 8/54* (2013.01); *G01S 7/5206* (2013.01)

(58) Field of Classification Search
None
See application file for complete search history.

(56) References Cited

U.S. PATENT DOCUMENTS

2004/0213372 A1* 10/2004 Akagi .................. A61B 6/4494
378/37
2016/0074012 A1 3/2016 Forzoni et al.
(Continued)

FOREIGN PATENT DOCUMENTS

JP 2016-059743 A 4/2016
JP 2018-043001 A 3/2018
(Continued)

OTHER PUBLICATIONS

"Decision to Grant a Patent" Office Action issued in JP 2022-551165; mailed by the Japanese Patent Office on Dec. 5, 2023.
(Continued)

*Primary Examiner* — Jonathan Cwern
(74) *Attorney, Agent, or Firm* — Studebaker & Brackett PC

(57) ABSTRACT

An ultrasound diagnostic apparatus includes an ultrasound probe, an image generation unit that generates an ultrasound image on which a breast of a subject is captured by performing transmission and reception of an ultrasound beam by using the ultrasound probe for the subject, a schema image generation unit that generates a schema image on which a region of interest is plotted based on a synthesized two-dimensional image generated by using a series of radiation images obtained by tomosynthesis imaging and on which the breast of the subject is captured, information on a tomosynthesis image accompanying the synthesized two-dimensional image and corresponding to the region of interest on the synthesized two-dimensional image, and information on the region of interest, and a monitor that displays the ultrasound image, the synthesized two-dimensional image, and the schema image.

18 Claims, 14 Drawing Sheets

(56) References Cited

U.S. PATENT DOCUMENTS

2018/0220994 A1\* 8/2018 Sugiyama .............. A61B 6/464
2018/0322633 A1\* 11/2018 Kuratomi ................. G06T 7/74
2021/0052247 A1\* 2/2021 Kobayashi ........... A61B 6/4441

FOREIGN PATENT DOCUMENTS

JP 2018-126204 A 8/2018
JP 2019-193788 A 11/2019

OTHER PUBLICATIONS

International Search Report issued in PCT/JP2021/028029 mailed Sep. 21, 2021.
International Preliminary Report On Patentability (Chapter I) and Written Opinion of the International Searching Authority issued in PCT/JP2021/028029; issued Mar. 28, 2023.

\* cited by examiner

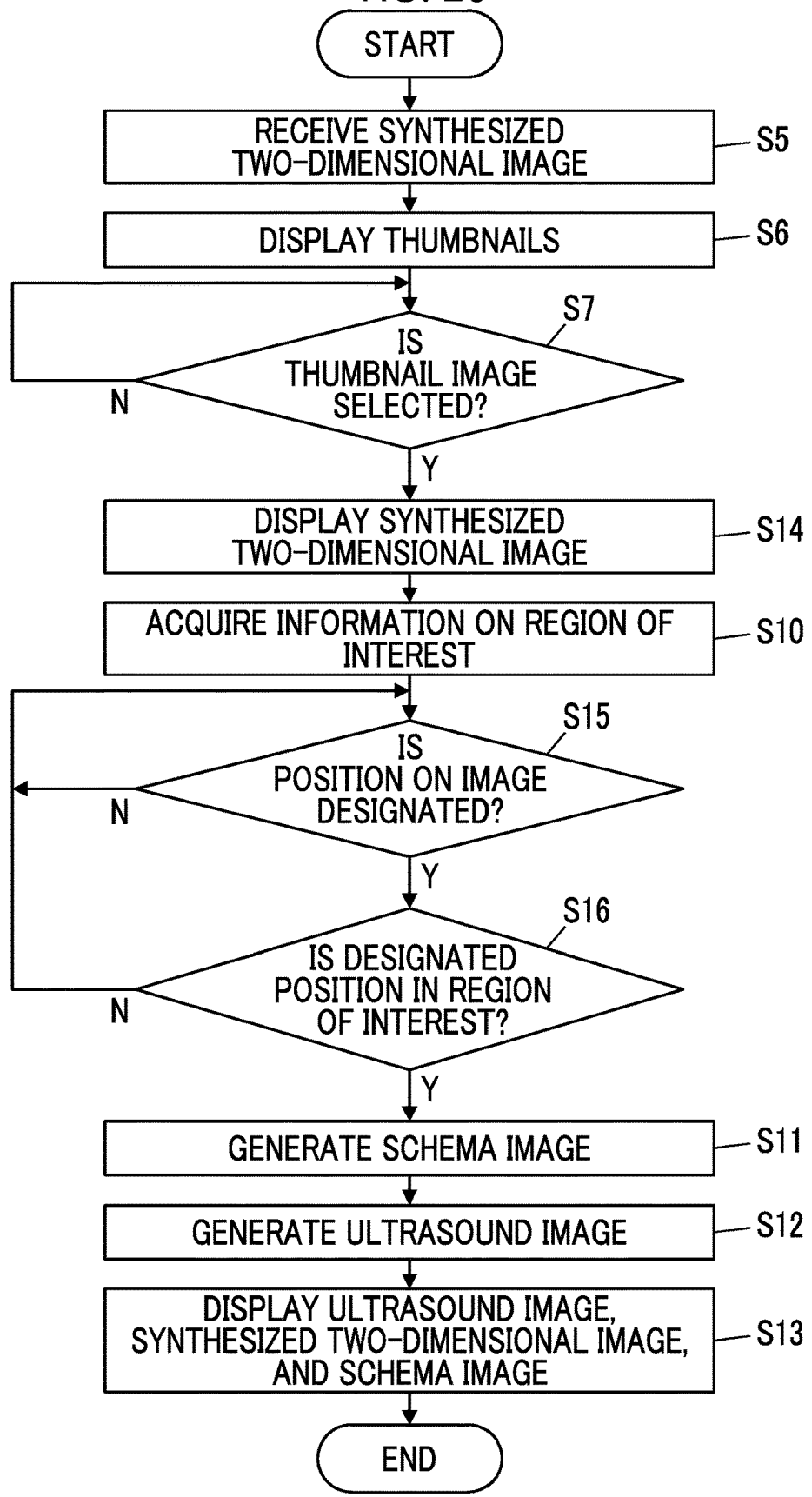

ULTRASOUND DIAGNOSTIC APPARATUS AND CONTROL METHOD OF ULTRASOUND DIAGNOSTIC APPARATUS

CROSS-REFERENCE TO RELATED APPLICATIONS

This application is a Continuation of PCT International Application No. PCT/JP2021/028029 filed on Jul. 29, 2021, which claims priority under 35 U.S.C. § 119(a) to Japanese Patent Application No. 2020-162405 filed on Sep. 28, 2020. The above applications are hereby expressly incorporated by reference, in its entirety, into the present application.

BACKGROUND OF THE INVENTION

1. Field of the Invention

The present invention relates to an ultrasound diagnostic apparatus having a function of displaying a synthesized two-dimensional image acquired by a mammography apparatus and a schema image on which a region of interest is plotted together with an ultrasound image, and a control method of an ultrasound diagnostic apparatus.

2. Description of the Related Art

In the related art, in a case where a region of interest of a breast that may be a lesion is detected by a mammography examination, a corresponding region of interest is subsequently searched for by an ultrasound examination while referring to a radiation image, and a qualitative diagnosis as to whether or not the region of interest of the breast included in an ultrasound image is the lesion may be performed.

As described above, in a case where the ultrasound examination is performed, there is a demand that the radiation image already captured by the mammography examination is desired to be referred to.

Here, the related arts related to the present invention include, for example, JP2018-43001A and JP2019-193788A.

JP2018-43001A discloses a medical information processing system for improving the efficiency of a workflow in a medical examination in which a tomosynthesis image and an ultrasound image are used in combination. A region of interest is set in a tomosynthesis image which is a three-dimensional image generated by performing imaging at different X-ray irradiation angles with respect to a breast of a subject, reference information in which positional information of the region of interest is associated with a schematic diagram of the breast is generated, and the tomosynthesis image and the reference information are displayed on a display.

JP2019-193788A discloses a medical information processing system that generates diagnostic support information of a subject based on an ultrasound image, an imaging position of the ultrasound image, and a mammography image. A region of interest is set on a mammography image which is a two-dimensional image, a straight line along an imaging direction including a position of the region of interest is drawn on a body mark of the breast, and the mammography image and the body mark of the breast are displayed as the diagnostic support information on a display.

SUMMARY OF THE INVENTION

In a case where the ultrasound examination is performed and in a case where there is the radiation image by the mammography examination captured before this examination, the radiation image is often confirmed. Normally, this confirmation work is performed by an image viewer connected to a server, but in a case where the confirmation work can be performed on an ultrasound apparatus, the workflow becomes efficient. Thus, it is desired to store the radiation image by the mammography examination in the ultrasound apparatus.

However, in the aspect in which the tomosynthesis image which is the three-dimensional image and the reference information are displayed on the display as in the medical information processing system of JP2018-43001A, it is necessary to transmit at least a plurality of slice images from the mammography apparatus or the server to the ultrasound apparatus and it is necessary to store the slice images in the ultrasound apparatus, and thus, there is a problem that a large-capacity storage area needs to be secured in the ultrasound apparatus.

In the aspect in which the mammography image which is the two-dimensional image and the body mark of the breast are displayed as the diagnostic support information on the display as in the medical information processing system of JP2019-193788A, even though the diagnostic support information is transmitted to the ultrasound apparatus, since three-dimensional distribution information of the breast is missing, there is a problem that it is difficult to perform an accurate diagnosis in the ultrasound apparatus.

The present invention has been made to solve such a conventional problem, and it is an object of the present invention to provide an ultrasound diagnostic apparatus and a control method of an ultrasound diagnostic apparatus capable of performing an accurate diagnosis on a region of interest of a breast without securing a large-capacity storage region.

In order to achieve the above object, an ultrasound diagnostic apparatus according to the present invention comprises an ultrasound probe, an image generation unit that generates an ultrasound image on which a breast of a subject is captured by performing transmission and reception of an ultrasound beam by using the ultrasound probe for the subject, a schema image generation unit that generates a schema image on which a region of interest is plotted based on a synthesized two-dimensional image generated by using a series of radiation images obtained by tomosynthesis imaging and on which the breast of the subject is captured, information on a tomosynthesis image accompanying the synthesized two-dimensional image and corresponding to the region of interest on the synthesized two-dimensional image, and information on the region of interest, and a monitor that displays the ultrasound image, the synthesized two-dimensional image, and the schema image.

The schema image generation unit can generate the schema image on which a plurality of the regions of interest on the synthesized two-dimensional image are plotted.

It is preferable that the ultrasound diagnostic apparatus further includes a region-of-interest list creation unit that creates a list of the regions of interest included in the synthesized two-dimensional image, and an input device in which a user performs an input operation. It is preferable that the list created by the region-of-interest list creation unit is displayed on the monitor, and the schema image generation unit generates the schema image on which the region of interest selected from the list displayed on the monitor by the user through the input device is plotted.

Alternatively, the ultrasound diagnostic apparatus can further include an input device in which a user performs an input operation. The synthesized two-dimensional image can be displayed on the monitor, and the schema image generation unit generates the schema image on which the region of interest is plotted in a case where any position designated by the user through the input device is included in the region of interest on the synthesized two-dimensional image displayed on the monitor.

It is preferable that the ultrasound diagnostic apparatus further includes a highlighting unit that highlights a region corresponding to the region of interest on the synthesized two-dimensional image and displays the region on the monitor in a case where the region of interest plotted on the schema image is designated by the user through the input device.

The highlighting unit can display a sub-window on the synthesized two-dimensional image, and displays the region of interest in an enlarged manner in the sub-window.

Alternatively, the highlighting unit can surround the region of interest on the synthesized two-dimensional image by a highlight line.

The schema image generation unit may generate the schema image including a slice line representing the tomosynthesis image corresponding to the region of interest.

The ultrasound diagnostic apparatus further includes an opinion display unit that displays an opinion for a mammography examination together with the schema image on the monitor.

Four synthesized two-dimensional images acquired by performing imaging in a cranio-caudal direction and imaging in a medio-lateral-oblique direction on each of left and right breasts of the subject can be displayed as thumbnails on the monitor in addition to the ultrasound image, the synthesized two-dimensional image, and the schema image.

In a case where a region of interest identical to the region of interest plotted on the schema image is captured on another synthesized two-dimensional image in which an imaging direction is different from an imaging direction of the synthesized two-dimensional image and the breast of the subject is captured, the synthesized two-dimensional image and the other synthesized two-dimensional image may be displayed together with the ultrasound image and the schema image on the monitor.

It is preferable that identification information of the region of interest, a position of the region of interest, a slice number of the tomosynthesis image corresponding to the region of interest, and an imaging angle are stored in a file that does not include a tag or an image accompanying the synthesized two-dimensional image.

It is preferable that the ultrasound diagnostic apparatus further includes a memory that stores the synthesized two-dimensional image.

A control method of an ultrasound diagnostic apparatus according to the present invention comprises generating an ultrasound image on which a breast of a subject is captured by performing transmission and reception of an ultrasound beam by using an ultrasound probe for the subject; generating a schema image on which a region of interest is plotted based on a synthesized two-dimensional image generated by using a series of radiation images obtained by tomosynthesis imaging and on which the breast of the subject is captured, information on a tomosynthesis image accompanying the synthesized two-dimensional image and corresponding to the region of interest on the synthesized two-dimensional image, and information on the region of interest, and displaying the ultrasound image, the synthesized two-dimensional image, and the schema image on a monitor.

According to the present invention, the schema image generation unit generates the schema image on which the region of interest is plotted based on the synthesized two-dimensional image generated by using the series of radiation images obtained by tomosynthesis imaging and on which the breast of the subject is captured, the information on the tomosynthesis image accompanying the synthesized two-dimensional image and corresponding to the region of interest on the synthesized two-dimensional image, and the information on the region of interest and the ultrasound image, the synthesized two-dimensional image, and the schema image are displayed on the monitor. Thus, it is possible to perform the accurate diagnosis on the region of interest of the breast without securing the large-capacity storage region.

BRIEF DESCRIPTION OF THE DRAWINGS

FIG. 23 is a flowchart showing an operation of the ultrasound diagnostic apparatus according to the fourth embodiment.

DESCRIPTION OF THE PREFERRED EMBODIMENTS

Hereinafter, embodiments of the present invention will be described with reference to the accompanying drawings.

Although configuration requirements to be described below may be described based on a representative embodiment of the present invention, the present invention is not limited to such an embodiment.

In the present specification, a numerical range represented by using "to" means a range including numerical values described before and after "to" as a lower limit and an upper limit.

In the present specification, "identical" and "same" include an error range generally allowed in a technical field.

First Embodiment

Figure 1:
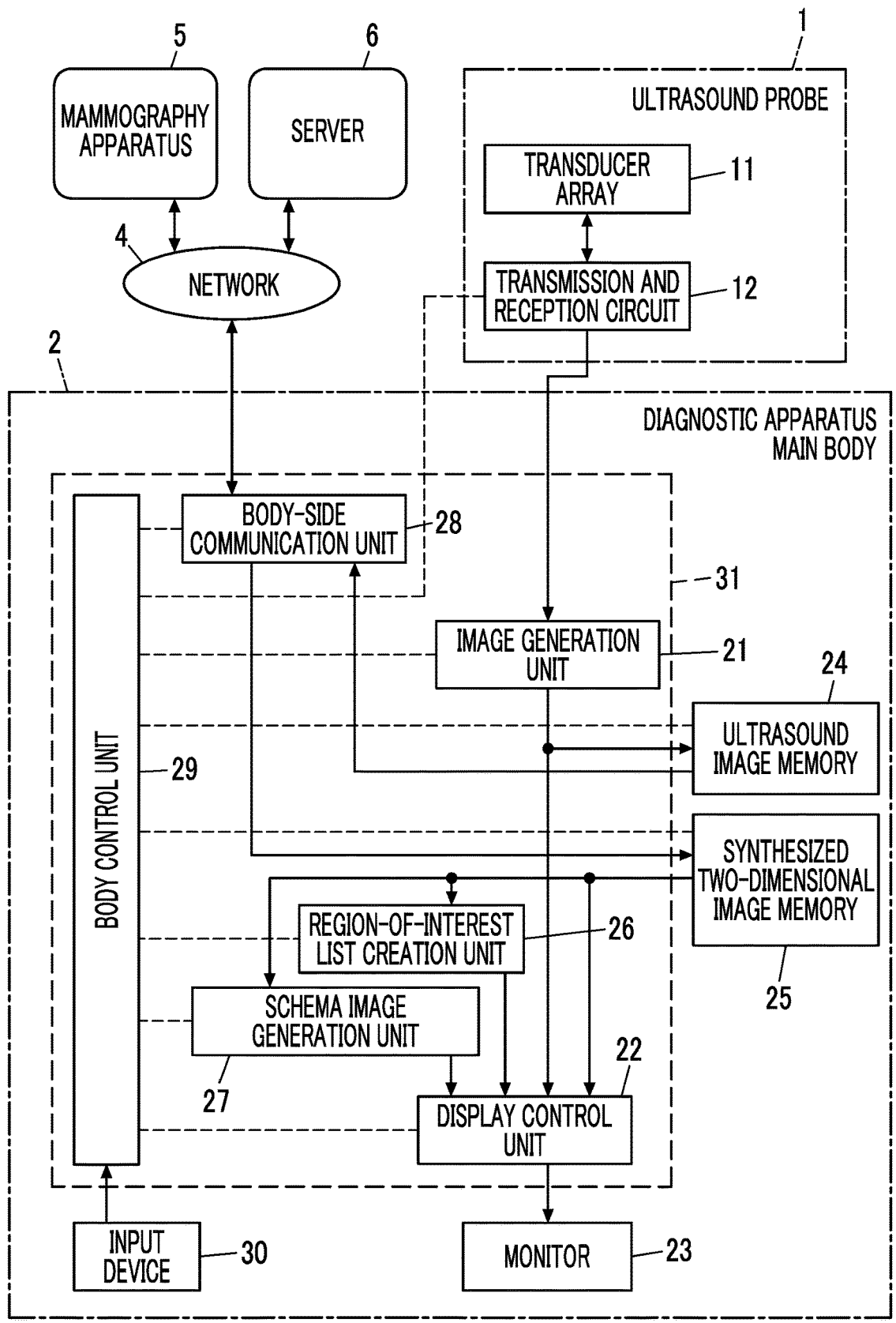
FIG. 1 is a block diagram showing a configuration of an ultrasound diagnostic apparatus according to a first embodiment of the present invention.

FIG. 1 shows a configuration of an ultrasound diagnostic apparatus according to a first embodiment of the present invention. The ultrasound diagnostic apparatus includes an ultrasound probe 1 and a diagnostic apparatus body 2. The ultrasound probe 1 and the diagnostic apparatus body 2 are connected to each other in a wired manner via a cable (not shown).

The ultrasound probe 1 includes a transducer array 11 and a transmission and reception circuit 12 connected to the transducer array 11.

The diagnostic apparatus body 2 has an image generation unit 21 connected to the transmission and reception circuit 12 of the ultrasound probe 1, a display control unit 22 and a monitor 23 are sequentially connected, and an ultrasound image memory 24 is connected to the image generation unit 21. The diagnostic apparatus body 2 has a synthesized two-dimensional image memory 25, a region-of-interest list creation unit 26 and a schema image generation unit 27 are connected to the synthesized two-dimensional image memory 25, and the synthesized two-dimensional image memory 25, the region-of-interest list creation unit 26 and the schema image generation unit 27 are connected to the display control unit 22.

The diagnostic apparatus body 2 has a body-side communication unit 28 connected to the synthesized two-dimensional image memory 25.

A body control unit 29 is connected to the image generation unit 21, the display control unit 22, the ultrasound image memory 24, the synthesized two-dimensional image memory 25, the region-of-interest list creation unit 26, the schema image generation unit 27, and the body-side communication unit 28, and an input device 30 is connected to the body control unit 29.

A body-side processor 31 includes the image generation unit 21, the display control unit 22, the region-of-interest list creation unit 26, the schema image generation unit 27, the body-side communication unit 28, and the body control unit 29.

A mammography apparatus 5 and a server 6 are connected to the body-side communication unit 28 of the diagnostic apparatus body 2 via a network 4.

The transducer array 11 of the ultrasound probe 1 includes a plurality of ultrasound oscillators arrayed one-dimensionally or two-dimensionally. Each of these oscillators transmits an ultrasound wave in response to a drive signal supplied from the transmission and reception circuit 12, receives a reflected wave from a subject, and outputs an analog received signal. For example, each oscillator is formed by forming electrodes at both ends of a piezoelectric substance including a piezoelectric ceramic represented by lead zirconate titanate (PZT), a polymer piezoelectric element represented by polyvinylidene difluoride (PVDF), and a piezoelectric single crystal represented by lead magnesium niobate-lead titanate (PMN-PT).

Figure 2:
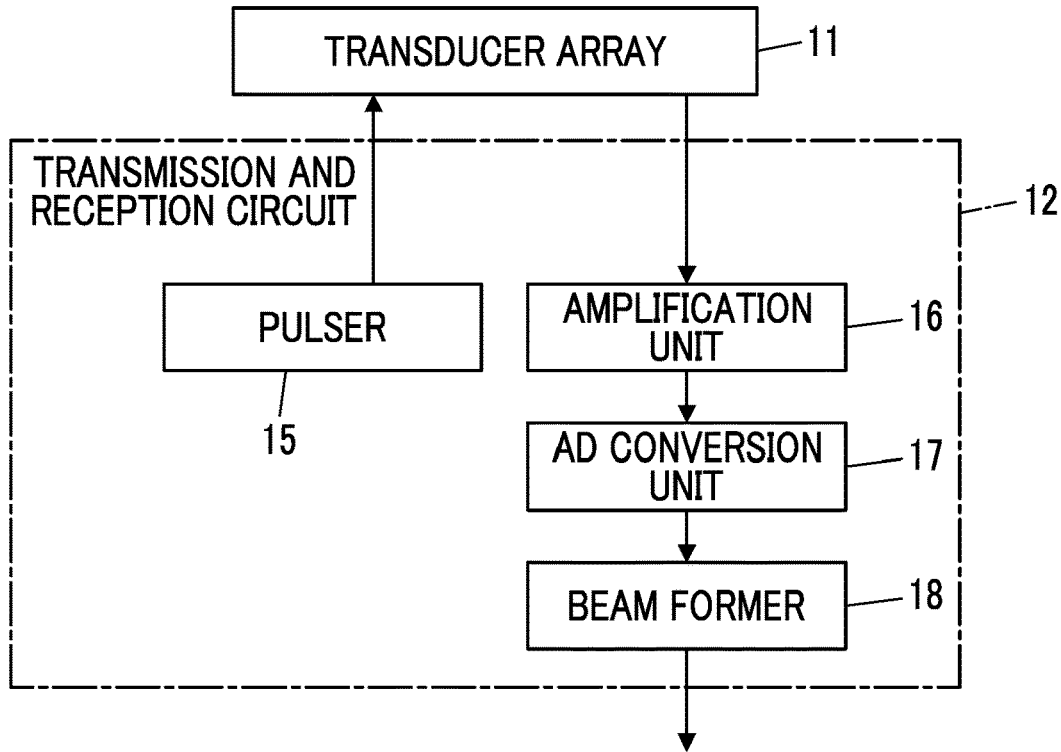
FIG. 2 is a block diagram showing an internal configuration of a transmission and reception circuit according to the first embodiment.

Under the control of a probe control unit 14, the transmission and reception circuit 12 transmits the ultrasound wave from the transducer array 11 and generates a sound ray signal based on a received signal acquired by the transducer array 11. As shown in FIG. 2, the transmission and reception circuit 12 includes a pulsar 15 connected to the transducer array 11, an amplification unit 16 sequentially connected in series to the transducer array 11, an analog to digital (AD) conversion unit 17, and a beamformer 18.

The pulsar 15 includes, for example, a plurality of pulse generators, and adjusts delay amounts of drive signals such that the ultrasound waves transmitted from the plurality of oscillators of the transducer array 11 form an ultrasound beam based on a transmission delay pattern selected in response to a control signal from the probe control unit 14, and transmits the drive signals to the plurality of oscillators. As described above, in a case where voltages having a pulsed or continuous wave shape are applied to the electrodes of the oscillators of the transducer array 11, the piezoelectric substance expands and contracts, ultrasound waves having a pulsed or continuous wave shape are generated from the oscillators, and an ultrasound beam is formed from a synthetic wave of these ultrasound waves.

The transmitted ultrasound beam is reflected by, for example, a target such as a site of the subject, and an ultrasound echo propagates toward the transducer array 11 of the ultrasound probe 1. The ultrasound echo propagating toward the transducer array 11 in this manner is received by the oscillators constituting the transducer array 11. At this time, the oscillators constituting the transducer array 11 expand and contract by receiving the propagating ultrasound echo, generate received signals which are electric signals, and output these received signals to the amplification unit 16.

The amplification unit 16 amplifies the signals input from the oscillators constituting the transducer array 11, and transmits the amplified signals to the AD conversion unit 17. The AD conversion unit 17 converts the signals transmitted from the amplification unit 16 into pieces of digital reception data, and transmits these pieces of reception data to the beamformer 18. The beamformer 18 performs so-called reception focus processing by delaying the pieces of reception data converted by the AD conversion unit 17 and adding the pieces of reception data according to a sound velocity or a sound velocity distribution set based on a reception delay pattern selected in response to a control signal from the probe control unit 14. By this reception focus processing, the pieces of reception data converted by the AD conversion unit 17 are phase-adjusted and added, and a sound ray signal in which a focal point of the ultrasound echo is narrowed down is acquired.

Figure 3:
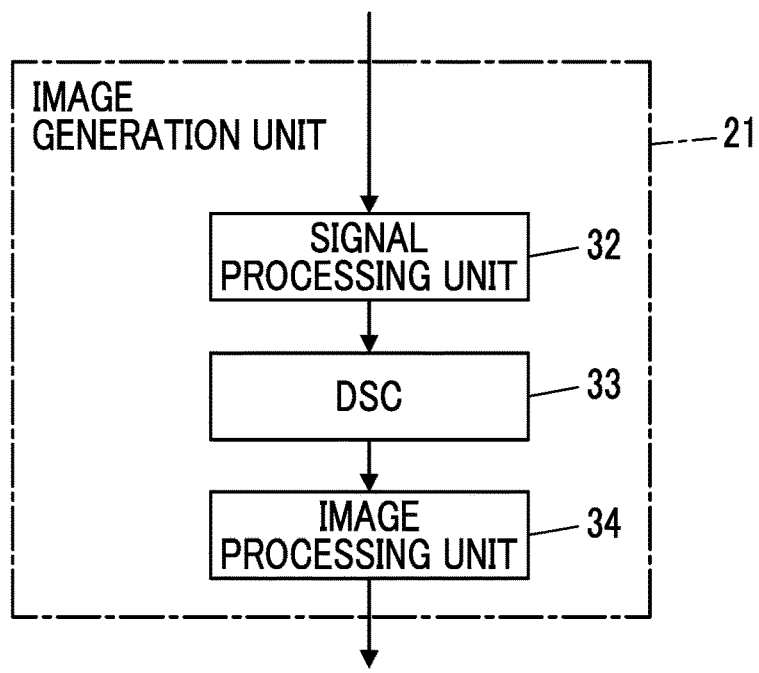
FIG. 3 is a block diagram showing an internal configuration of an image generation unit according to the first embodiment.

As shown in FIG. 3, the image generation unit 21 of the diagnostic apparatus body 2 has a configuration in which a signal processing unit 32, a digital scan converter (DSC) 33, and an image processing unit 34 are sequentially connected in series.

The signal processing unit 32 generates an ultrasound image signal (B-mode image signal) which is tomographic image information about a tissue in a subject T by performing correction of attenuation due to a distance on the sound ray signal sent from the body-side communication unit 28 in response to a depth of a reflection position of the ultrasound wave and performing envelope detection processing.

The DSC 33 converts the ultrasound image signal generated by the signal processing unit 32 into an image signal according to a method for scanning a normal television signal (raster conversion).

The image processing unit 34 performs various kinds of necessary image processing such as gradation processing on the ultrasound image signal input from the DSC 33, and then outputs a signal indicating the ultrasound image to the display control unit 22 and the ultrasound image memory 24. The signal indicating the ultrasound image generated by the image generation unit 21 in this manner is simply referred to as the ultrasound image.

The display control unit 22 performs predetermined processing on the ultrasound image sent from the image generation unit 21 under the control of the body control unit 29, and displays the ultrasound image on the monitor 23.

The monitor 23 displays the ultrasound image under the control of the display control unit 22 and includes, for example, a display device such as a liquid crystal display (LCD) or an organic electroluminescence display (organic EL display).

The ultrasound image memory 24 is a memory that stores the ultrasound image generated by the image generation unit 21 under the control of the body control unit 29. For example, the ultrasound image memory 24 can store the series of ultrasound images of a plurality of frames generated by the image generation unit 21 in response to the diagnosis of breasts of the subject.

The synthesized two-dimensional image memory 25 stores the synthesized two-dimensional image received from the mammography apparatus 5 or the server 6 by the body-side communication unit 28 via the network 4. The synthesized two-dimensional image is generated in the mammography apparatus 5 based on the series of radiation images obtained by tomosynthesis imaging, and is stored in the server 6. For example, four synthesized two-dimensional images including a synthesized two-dimensional image R-CC in a cranio-caudal (CC) direction and a synthesized two-dimensional image R-MLO in a medio-lateral-oblique (MLO) direction of a right breast of the subject and a synthesized two-dimensional image L-CC in the CC direction and a synthesized two-dimensional image L-MLO in the MLO direction of a left breast are generated, and these four synthesized two-dimensional images are transmitted to the body-side communication unit 28 from the mammography apparatus 5 or the server 6 and are stored in the synthesized two-dimensional image memory 25.

Examples of the ultrasound image memory 24 and the synthesized two-dimensional image memory 25 include recording media such as a flash memory, a hard disc drive (HDD), a solid state drive (SSD), a flexible disc (FD), a magneto-optical (MO) disc, a magnetic tape (MT), a random access memory (RAM), a compact disc (CD), a digital versatile disc (DVD), a secure digital card (SD card), and a universal serial bus (USB) memory.

The region-of-interest list creation unit 26 creates a list of regions of interest included in the synthesized two-dimensional image. The list of regions of interest created by the region-of-interest list creation unit 26 is displayed on the monitor 23 through the display control unit 22.

The schema image generation unit 27 generates a schema image to be described below that schematically represents the breasts. The schema image generated by the schema image generation unit 27 is displayed on the monitor 23 through the display control unit 22.

Under the control of the body control unit 29, the body-side communication unit 28 sends the ultrasound image generated by the image generation unit 21 and stored in the ultrasound image memory 24 to the server 6 via the network 4.

Under the control of the body control unit 29, the body-side communication unit 28 receives the synthesized two-dimensional image transmitted from the mammography apparatus 5 or the server 6 via the network 4 and sends the received synthesized two-dimensional image to the synthesized two-dimensional image memory 25.

The input device 30 is for a user to perform an input operation, and includes, for example, a device such as a keyboard, a mouse, a track ball, a touch pad, and a touch sensor disposed on the monitor 23 in a superimposed manner.

The body control unit 29 controls each unit of the diagnostic apparatus body 2 based on a control program or the like stored in advance.

Although not shown, a body-side storage unit is connected to the body control unit 29. The body-side storage unit stores a control program or the like of the diagnostic apparatus body 2. Examples of the body-side storage unit include a flash memory, a random access memory (RAM), a secure digital card (SD card), and a solid state drive (SSD).

The body-side processor 31 including the image generation unit 21, the display control unit 22, the region-of-interest list creation unit 26, the schema image generation unit 27, the body-side communication unit 28, and the body control unit 29 may include a central processing unit (CPU) and a control program causing the CPU to perform various kinds of processing, and includes a field programmable gate array (FPGA), a digital signal processor (DSP), an application specific integrated circuit (ASIC), a graphics processing unit (GPU), or other integrated circuits (ICs), or a combination thereof.

The image generation unit 21, the display control unit 22, the region-of-interest list creation unit 26, the schema image generation unit 27, the body-side communication unit 28, and the body control unit 29 of the body-side processor 31 can also be integrated into one CPU or the like in whole or in part.

Figure 4:
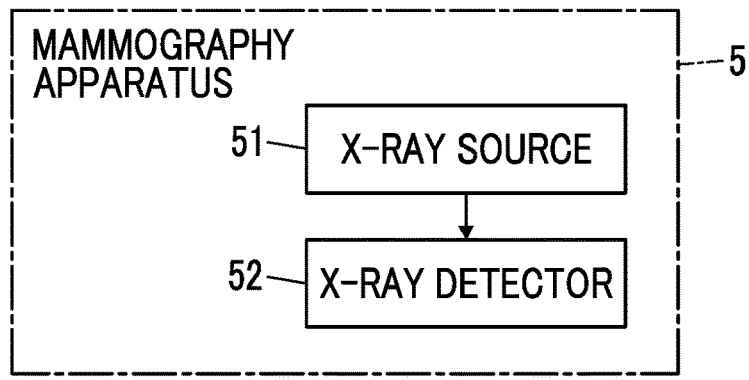
FIG. 4 is a block diagram showing a configuration of a mammography examination connected to an ultrasound diagnostic apparatus via a network.

As shown in FIG. 4, the mammography apparatus 5 connected to the diagnostic apparatus body 2 via the network 4 includes an X-ray source 51 and an X-ray detector 52.

For example, the series of radiation images are acquired by tomosynthesis imaging by irradiating the breasts of the subject in a state of being compressed by a compression plate (not shown) with X-rays from the X-ray source 51 while an X-ray incidence angle is changed and detecting the X-rays transmitted through the breasts by the X-ray detector 52.

Figure 5:
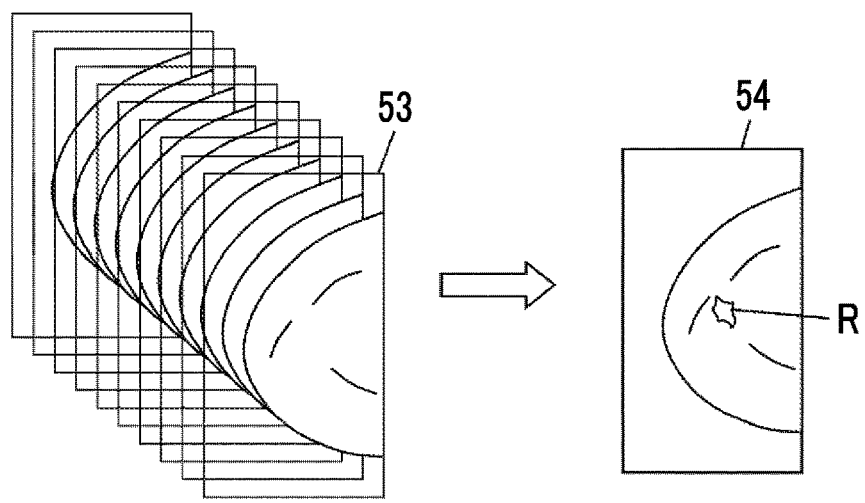
FIG. 5 is a diagram conceptually showing a method of generating a synthesized two-dimensional image.

The mammography apparatus 5 further includes a computer (not shown) mounted thereon, and the synthesized two-dimensional images can be generated by the computer. That is, as shown in FIG. 5, a plurality of tomosynthesis images 53 are generated by three-dimensionally reconstructing the series of radiation images acquired by tomosynthesis imaging, and a synthesized two-dimensional image 54 is generated based on the plurality of tomosynthesis images 53.

The plurality of tomosynthesis images 53 are, for example, a plurality of tomographic images obtained by slicing the breasts in parallel with each other at a slight interval of about 1 mm.

The mammography apparatus 5 can also generate the synthesized two-dimensional image 54 from the series of radiation images acquired by tomosynthesis imaging without using the plurality of tomosynthesis images 53 that are three-dimensionally reconstructed. In a case where the synthesized two-dimensional image 54 is generated, information on a region of interest R extracted by CAD processing to be described later may be reflected and generated. For example, the synthesized two-dimensional image 54 can be generated to further highlight the region of interest R.

As computer-aided detection (CAD) processing of the mammography apparatus 5, the detection of the region of interest R is performed on each of the plurality of reconstructed tomosynthesis images 53.

For example, the region of interest R can be detected from the tomosynthesis image 53 by deep learning utilizing artificial intelligence (AI).

The CAD processing can be performed by the computer mounted on the mammography apparatus 5, or can be performed by a computer dedicated to the CAD processing connected to the mammography apparatus 5.

The synthesized two-dimensional image 54 is represented as, for example, image data in a so-called digital imaging and communications in medicine (DICOM) format to which patient identification information is attached, and has a tag for storing accessory information. In any of the tomosynthesis images 53 among the plurality of tomosynthesis images 53, in a case where the region of interest R is detected by the CAD processing, the information on the detected region of interest R and information on the tomosynthesis image 53 corresponding to the region of interest R are stored in the tag of the synthesized two-dimensional image 54. Specifically, identification information of the detected region of interest R, a position of the region of interest R, a slice number of the tomosynthesis image 53 corresponding to the region of interest R and best representing the region of interest R, and the like are stored in the tag.

In the case of the synthesized two-dimensional image 54 in the MLO direction, an imaging angle during imaging by the mammography apparatus 5, that is, an angle at which the X-ray detector 52 is installed is stored in the positioner primary angle (PPA) which is a public tag of DICOM.

As the CAD processing of the mammography apparatus 5, in a case where the synthesized two-dimensional image 54 is generated from the series of radiation images captured by tomosynthesis imaging, the detection of the region of interest R can be performed on the series of radiation images captured by tomosynthesis imaging instead of the plurality of reconstructed tomosynthesis images 53. However, it is necessary to convert the detected position of the region of interest R into a position in the three-dimensionally reconstructed tomosynthesis image 53, then convert the position into a slice number of the tomosynthesis image 53, and store the slice number in the tag of the synthesized two-dimensional image 54.

A DICOM tag can be used as the tag of the synthesized two-dimensional image 54. Various kinds of information such as a slice number corresponding to the region of interest R can be stored in the DICOM tag. A service objective pair instance unique identifier (SOP instance UID) of another image can be stored in the DICOM tag. A study instance unique identifier (Study Instance UID) and a series instance unique identifier (Series Instance UID) of another image in a DICOM standard can also be stored.

The information on the detected region of interest R and the information on the tomosynthesis image 53 corresponding to the region of interest R is not stored in the tag of the synthesized two-dimensional image 54, and can also be stored in, for example, a file such as DICOM-structured report (SR) in which only data that does not include the image is stored.

By doing this, the plurality of reconstructed tomosynthesis images 53 and the generated synthesized two-dimensional image 54 are sent from the mammography apparatus 5 to the server 6 via the network 4. The series of radiation images acquired by tomosynthesis imaging may be sent from the mammography apparatus 5 to the server 6 via the network 4.

The server 6 connected to the diagnostic apparatus body 2 via the network 4 stores various kinds of image data generated by the ultrasound diagnostic apparatus and the mammography apparatus 5. Specifically, the ultrasound image generated by the diagnostic apparatus body 2, the plurality of tomosynthesis images 53 generated by the mammography apparatus 5, and the synthesized two-dimensional image 54 are stored in the server 6. The series of radiation images acquired by tomosynthesis imaging in the mammography apparatus 5 can also be stored in the server 6. In this case, as will be described later, the server 6 may have a function of reconstruction processing and generating the synthesized two-dimensional image 54.

The server 6 can be used as a server in a so-called picture archiving and communication system (PACS).

Figure 6:
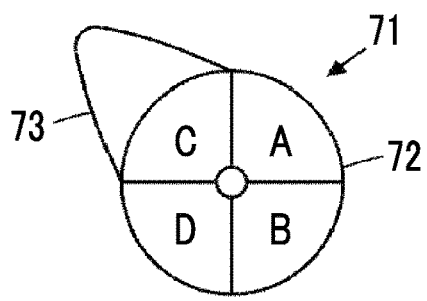
FIG. 6 is a diagram showing an example of a schema image.

FIG. 6 shows a schema image 71 generated by the schema image generation unit 27 of the diagnostic apparatus body 2. The schema image 71 shown in FIG. 6 schematically represents the right breast as viewed from the front, and has a circular breast region 72 and a substantially triangular armpit region 73 that represents an armpit and extends obliquely upward from the breast region 72. The breast region 72 is divided into four regions of an inner upper region A, an inner lower region B, an outer upper region C, and an outer lower region D of the breast, and the armpit region 73 is connected to an upper portion obliquely leftward of the outer upper region C.

The schema image 71 shown in FIG. 6 is reversed left and right, a schema image schematically representing the left breast is obtained.

Figure 7:
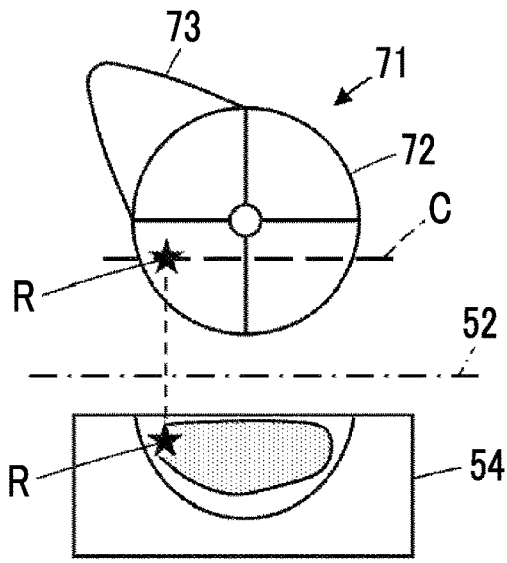
FIG. 7 is a diagram showing a schema image corresponding to a synthesized two-dimensional image in a cranio-caudal (CC) direction.

As shown in FIG. 7, the region of interest R is plotted on the schema image 71 generated by the schema image generation unit 27, and a slice line C indicating the tomosynthesis image 53 that best represents the region of interest R is drawn. The schema image generation unit 27 can generate the schema image 71 on which the region of interest R is plotted and the slice line C is drawn by referring to accessory information stored in the DICOM-SR or the tag of the synthesized two-dimensional image 54, that is, the identification information of the region of interest R, the position of the region of interest R, the slice number of the tomosynthesis image 53 that best represents the region of interest R, the imaging angle, and the like.

First, the schema image generation unit 27 draws the slice line C on the schema image 71 based on the imaging angle and the slice number of the tomosynthesis image 53 that best represents the region of interest R, which are stored in the DICOM-SR or the tag of the synthesized two-dimensional image 54. The slice line C has the same imaging angle and is drawn as a straight line extending in parallel with the X-ray detector 52.

Figure 8:
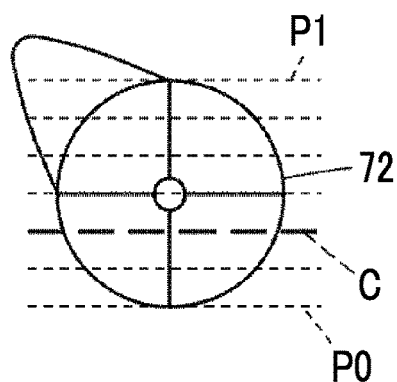
FIG. 8 is a diagram showing a method of drawing a slice line on a schema image corresponding to the synthesized two-dimensional image in the CC direction.

At this time, for example, in a case where the synthesized two-dimensional image 54 is the synthesized two-dimensional image R-CC in the CC direction of the right breast, since the imaging angle is "0 degree", slice planes by the tomosynthesis images 53 extend in a horizontal direction. Thus, as shown in FIG. 8, it is assumed that a slice plane P0 by the first tomosynthesis image 53 among the plurality of tomosynthesis images 53 is positioned at a lowermost part of the circular breast region 72 of the schema image 71, and the circular breast region is formed. It is assumed that a slice plane P1 by the last tomosynthesis image 53 among the plurality of tomosynthesis images 53 is positioned at an uppermost part of the circular breast region 72, and a space between the slice plane P0 and the slice plane P1 is equally divided in accordance with the number of tomosynthesis images 53. The slice line C representing the slice plane by the tomosynthesis image 53 that best represents the region of interest R at a position corresponding to the slice number of the tomosynthesis image 53 stored in the DICOM-SR or the tag of the synthesized two-dimensional image 54 from the slice plane P0 of the first tomosynthesis image 53 is drawn.

For example, it is assumed that the number of tomosynthesis images 53 is 7 and the slice number of the tomosynthesis image 53 that best represents the region of interest R is "3", the space between the slice plane P0 and the slice plane P1 is equally divided into six parts, and the slice line C is drawn at a position of the third slice plane corresponding to the slice number from the first slice plane P0 positioned at the lowermost part of the circular breast region 72.

The number of tomosynthesis images 53 can be stored in the DICOM-SR or the tag of the synthesized two-dimensional image 54.

Instead of storing the number of tomosynthesis images 53 in the DICOM-SR or the tag of the synthesized two-dimensional image 54, the number of tomosynthesis images 53 to be generated may be calculated based on a thickness of the breast compressed by the compression plate during imaging of the radiation image, a slice thickness, and a slice interval.

Further, setting can be performed such that the first slice plane P0 is positioned at the uppermost part of the circular breast region 72 and the last slice plane P1 is positioned at the lowermost part of the circular breast region 72.

In a case where the slice line C is drawn in this manner, the schema image generation unit 27 subsequently projects a contour of the region of interest R in the synthesized two-dimensional image 54 onto the slice line C in a state where the synthesized two-dimensional image 54 and the schema image 71 are positioned with each other. Accordingly, the position of the region of interest R on the slice line C is specified, and as shown in FIG. 7, the schema image 71 on which the slice line C is drawn and the region of interest R is plotted on the slice line C is generated.

Although the schema image 71 shown in FIG. 7 corresponds to the synthesized two-dimensional image R-CC in the CC direction of the right breast, the schema image 71 corresponding to the synthesized two-dimensional image R-MLO in the MLO direction of the right breast can also be similarly generated.

Figure 9:
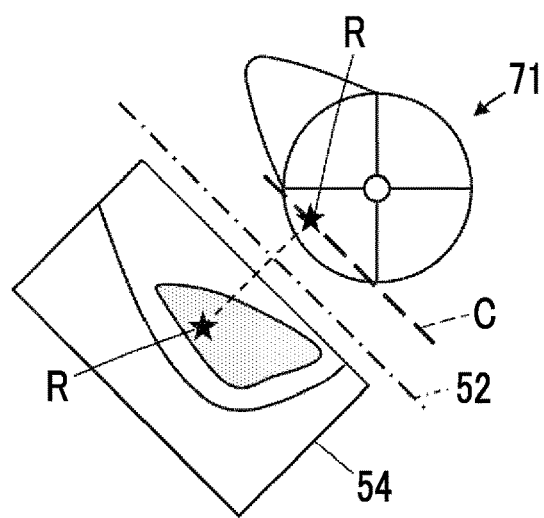
FIG. 9 is a diagram showing a schema image corresponding to a synthesized two-dimensional image in a medio-lateral-oblique (MLO) direction.

As shown in FIG. 9, in the synthesized two-dimensional image 54 in the MLO direction, an angle of the X-ray detector 52 during imaging is stored as the imaging angle in the public tag PPA of the synthesized two-dimensional image 54, and the slice line C becomes the straight line inclined in accordance with the imaging angle.

Figure 10:
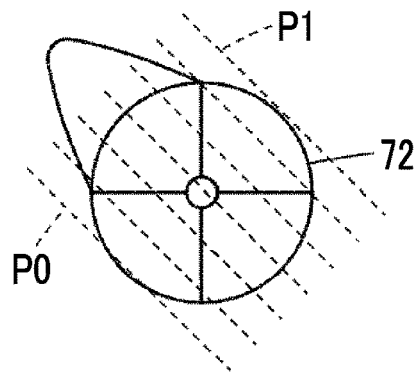
FIG. 10 is a diagram showing a method of drawing a slice line on a schema image corresponding to the synthesized two-dimensional image in the MLO direction.

Thus, as shown in FIG. 10, two of the slice plane P0 and the slice plane P1 inclined in accordance with the imaging angle may be positioned to sandwich the circular breast region 72 of the schema image 71, the space between the slice plane P0 and the slice plane P1 may be equally divided in accordance with the number of tomosynthesis images 53, and the slice line C may be drawn at the position corresponding to the slice number of the tomosynthesis image 53 stored in the DICOM-SR or the tag of the synthesized two-dimensional image 54.

The contour of the region of interest R in the synthesized two-dimensional image 54 is projected onto the slice line C, and thus, the schema image 71 corresponding to the synthesized two-dimensional image R-MLO in the MLO direction of the right breast, on which the slice line C is drawn and the region of interest R is plotted on the slice line C, is generated as shown in FIG. 9.

Figure 11:
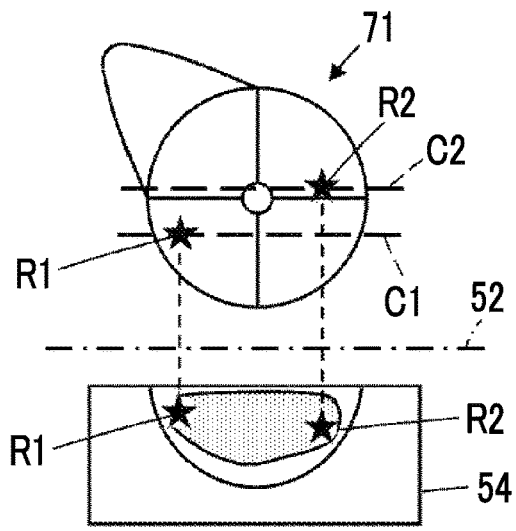
FIG. 11 is a diagram showing a schema image corresponding to a synthesized two-dimensional image having a plurality of regions of interest in the CC direction.
Figure 12:
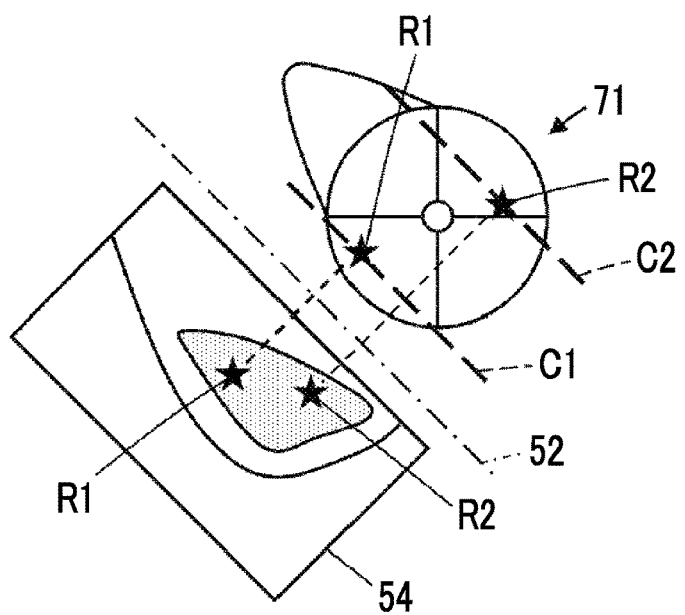
FIG. 12 is a diagram showing a schema image corresponding to a synthesized two-dimensional image having a plurality of regions of interest in the MLO direction.

As shown in FIGS. 11 and 12, in a case where the synthesized two-dimensional image 54 has a plurality of regions of interest R1 and R2, slice lines C1 and C2 corresponding to the plurality of regions of interest R1 and R2, respectively, are similarly drawn, and the schema image 71 on which the regions of interest R1 and R2 are plotted on the slice lines C1 and C2 is generated.

The schema image 71 shown in FIG. 11 corresponds to the synthesized two-dimensional image R-CC in the CC direction of the right breast, and the schema image 71 shown in FIG. 12 corresponds to the synthesized two-dimensional image R-MLO in the MLO direction of the right breast.

Although not shown, the schema image corresponding to the synthesized two-dimensional image L-CC in the CC direction of the left breast and the schema image corresponding to the synthesized two-dimensional image L-MLO in the MLO direction of the left breast are also reversed left and right with respect to the left-right inverted from the schema image 71 for the right breast, but can be similarly generated.

Although the plurality of regions of interest R1 and R2 are described in the list of regions of interest created by the region-of-interest list creation unit 26, only the selected region of interest can be plotted in the schema image 71 among the plurality of regions of interest R1 and R2 described in the list of regions of interest, or all the regions of interest can be plotted on the schema image 71.

Next, an operation of the ultrasound diagnostic apparatus according to the first embodiment will be described.

Figure 13:
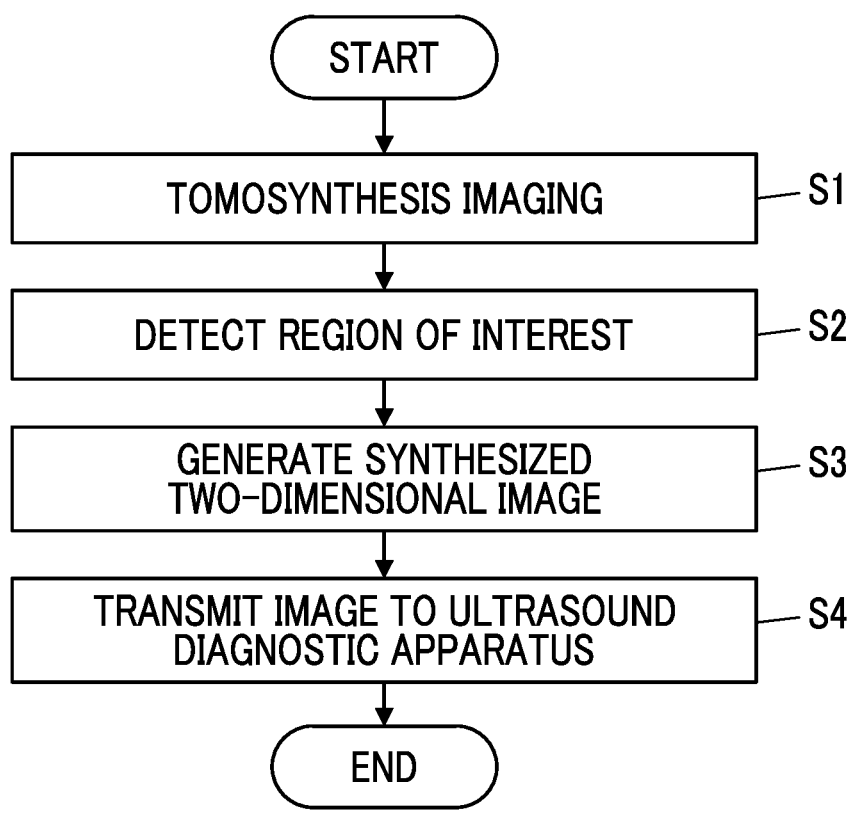
FIG. 13 is a flowchart showing an operation of a mammography apparatus.

As shown in a flowchart of FIG. 13, the mammography apparatus 5 performs imaging on the breasts of the subject in advance, and the synthesized two-dimensional image 54 is generated. That is, in step S1, tomosynthesis imaging is performed by irradiating the breasts of the subject in a state of being compressed by a compression plate (not shown) with X-rays from the X-ray source 51 while the X-ray incidence angle is changed, and the series of radiation images are acquired. The plurality of tomosynthesis images 53 are generated by three-dimensionally reconstructing the acquired series of radiation images.

In subsequent step S2, as the CAD processing of the mammography apparatus 5, the detection of the region of interest R is performed on each of the plurality of tomosynthesis images 53 that are three-dimensionally reconstructed.

In step S3, the synthesized two-dimensional image 54 is generated based on the plurality of tomosynthesis images 53. The synthesized two-dimensional image 54 includes the tag in which the identification information of the detected region of interest R, the position of the region of interest R, the slice number of the tomosynthesis image 53 that best represents the region of interest R, and the like are stored, and is represented as the image data having the tag in which the imaging angle during tomosynthesis imaging is stored in the case of the synthesized two-dimensional image 54 in the MLO direction. Alternatively, the identification information of the region of interest R, the position of the region of interest R, the slice number of the tomosynthesis image 53 that best represents the region of interest R, the imaging angle during tomosynthesis imaging, and the like are stored in the DICOM-SR.

The series of radiation images, the plurality of tomosynthesis images 53, and the synthesized two-dimensional image 54 acquired by the mammography apparatus 5 are sent from the mammography apparatus 5 to the server 6 via the network 4 and are stored by the server 6.

In step S4, in a case where inquiry and reception of the synthesized two-dimensional image 54 is requested from the user of the ultrasound diagnostic apparatus based on patient identification information, the synthesized two-dimensional image 54 is transmitted to the diagnostic apparatus body 2 of the ultrasound diagnostic apparatus from the mammography apparatus 5 or the server 6 via the network 4. For example, four synthesized two-dimensional images including the synthesized two-dimensional image R-CC in the CC direction and the synthesized two-dimensional image R-MLO in the MLO direction of the right breast of the subject and the synthesized two-dimensional image L-CC in the CC direction and the synthesized two-dimensional image L-MLO in the MLO direction of the left breast are transmitted to the diagnostic apparatus body 2 of the ultrasound diagnostic apparatus. The mammography apparatus 5 can also automatically transmit the synthesized two-dimensional image 54 to the set ultrasound diagnostic apparatus without receiving the request from the user of the ultrasound diagnostic apparatus.

Figure 14:
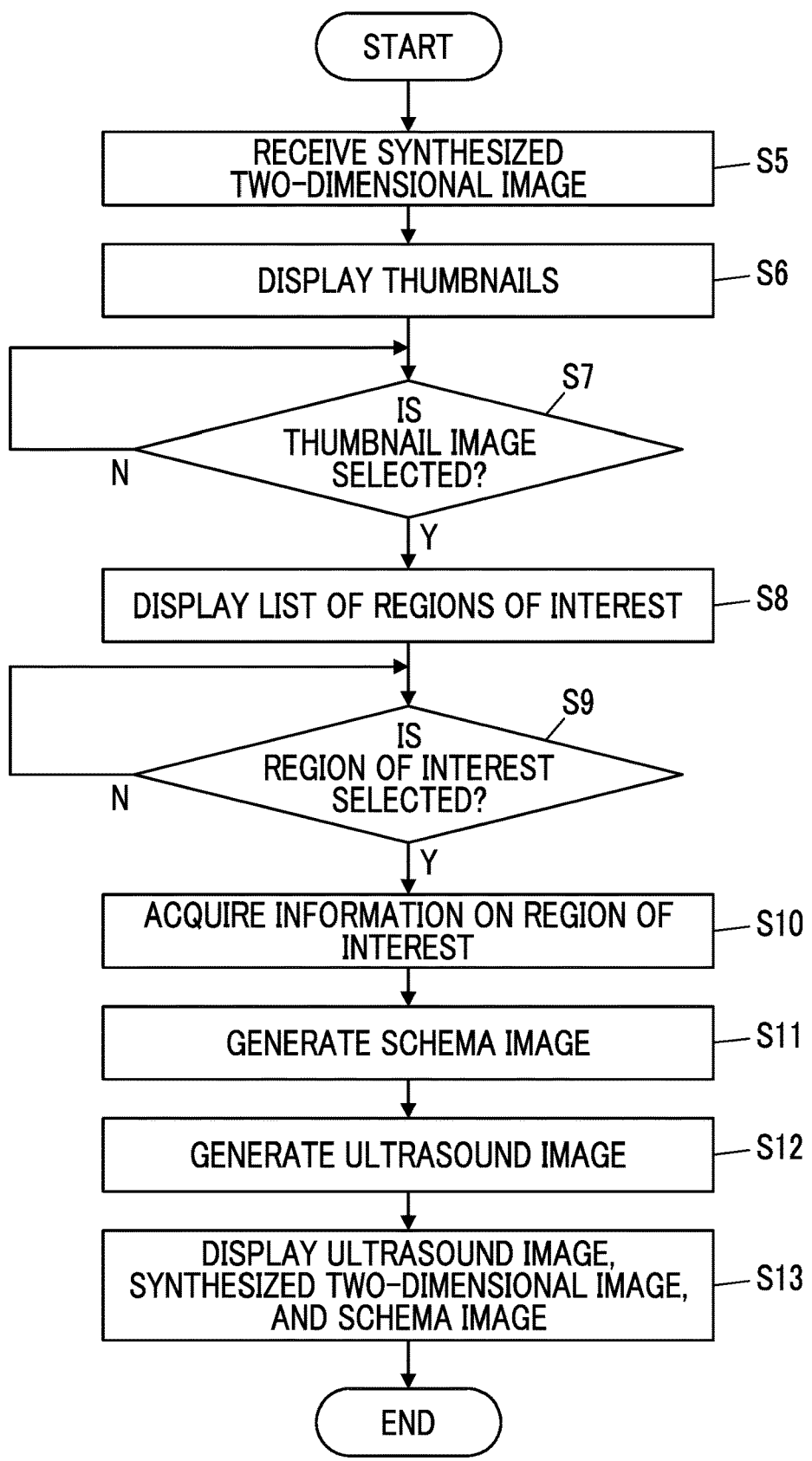
FIG. 14 is a flowchart showing an operation of the ultrasound diagnostic apparatus according to the first embodiment.

In the ultrasound diagnostic apparatus, as shown in a flowchart of FIG. 14, in step S5, the synthesized two-dimensional image 54 is received from the mammography apparatus 5 or the server 6 via the network 4 by the body-side communication unit 28 of the diagnostic apparatus body 2 and is stored in the synthesized two-dimensional image memory 25.

Figure 15:
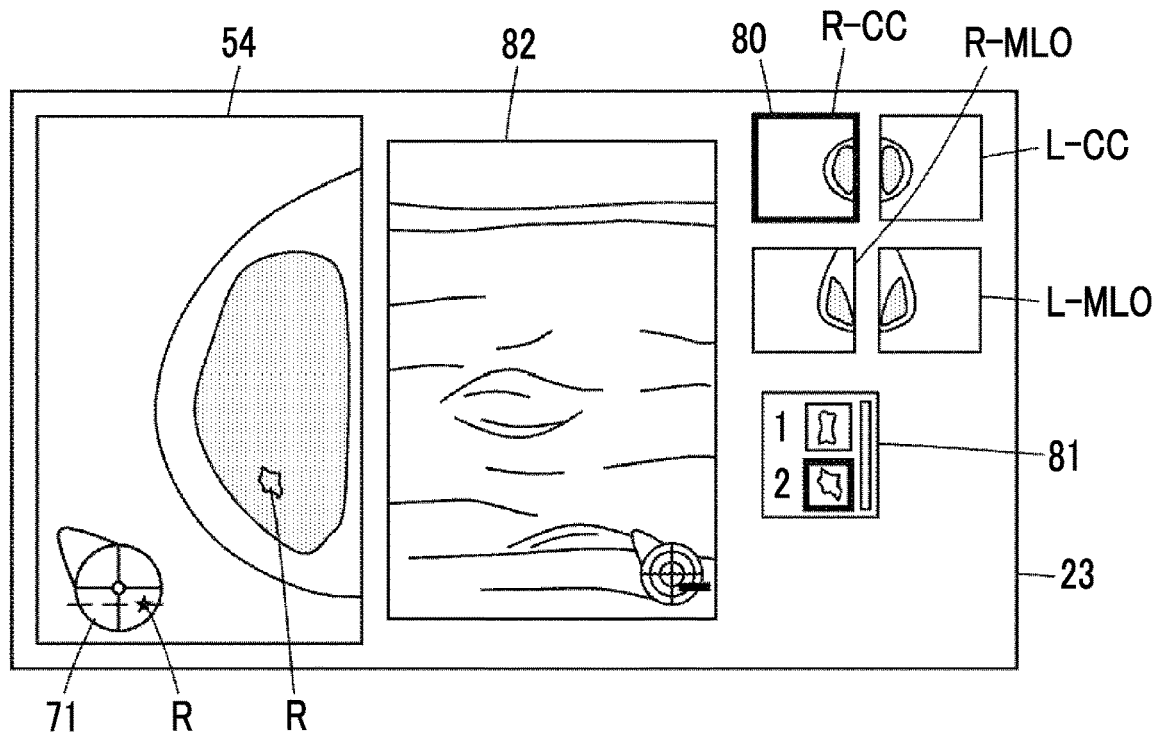
FIG. 15 is a diagram showing a display example of a monitor in the ultrasound diagnostic apparatus according to the first embodiment.

In subsequent step S6, for example, the body control unit 29 of the diagnostic apparatus body 2 displays, as thumbnails, four synthesized two-dimensional images 54 including R-CC, R-MLO, L-CC, and L-MLO received by the body-side communication unit 28 on the monitor 23. In FIG. 15, thumbnail images 80 corresponding to four synthesized two-dimensional images R-CC, R-MLO, L-CC, and L-MLO are represented in an upper right portion of the monitor 23.

In a case where one of the thumbnail images 80 corresponding to four synthesized two-dimensional images R-CC, R-MLO, L-CC, and L-MLO is selected by the user in step S7, the region-of-interest list creation unit 26 creates a list 81 of regions of interest R and displays the list on the monitor 23 in step S8. At this time, the region-of-interest list creation unit 26 creates the list 81 of regions of interest R included in the synthesized two-dimensional image 54 by referring to the DICOM-SR or the tag of the synthesized two-dimensional image 54 corresponding to the thumbnail image 80 selected by the user from among the thumbnail images 80 corresponding to four synthesized two-dimensional images R-CC, R-MLO, L-CC, and L-MLO, and displays the list 81 of regions of interest R on the monitor 23 through the display control unit 22.

In a case where one region of interest R is selected from the list 81 of regions of interest R by the user in step S9, the schema image generation unit 27 acquires information about the selected region of interest R by referring to the DICOM-SR or the tag of the synthesized two-dimensional image 54 in step S10, and generates the schema image 71 in step S11. Specifically, information such as the identification information of the region of interest R selected by the user, the position of the region of interest R, the slice number of the tomosynthesis image 53 that best represents the region of interest R, the imaging angle, and the like is acquired by the schema image generation unit 27 from the DICOM-SR or the tag of the synthesized two-dimensional image 54, and the schema image 71 on which the slice line C is drawn and the region of interest R is plotted on the slice line C.

The schema image 71 generated in this manner is displayed on the monitor 23 together with the synthesized two-dimensional image 54 corresponding to the thumbnail image 80 selected by the user.

In advance, the information such as the identification information of the region of interest R, the position of the region of interest R, the slice number of the tomosynthesis image 53 that best represents the region of interest R, the imaging angle, and the like may be registered in a database in association with the patient identification information, and the information may be acquired from the database by the schema image generation unit 27 in a case where one region of interest R is selected from the list 81 of regions of interest R by the user.

A position of a geometric center of the region of interest R or a position of a centroid of the region of interest R can be used as the position of the region of interest R. A major axis and a minor axis of the region of interest R can also be stored as the information about the region of interest R in the DICOM-SR or the tag of the synthesized two-dimensional image 54.

After the schema image 71 is displayed on the monitor 23, in subsequent step S12, the user captures the ultrasound image of the breast of the subject.

At this time, the ultrasound probe 1 is brought into contact with a surface of the breast of the subject, and the transmission and reception of the ultrasound waves directed into the subject from the plurality of oscillators of the transducer array 11 in response to the drive signals from the pulsar 15 of the transmission and reception circuit 12 is started. The ultrasound echo due to the tissue in the subject is received by the plurality of oscillators of the transducer array 11, the received signal which is the analog signal is output to the amplification unit 16 and is amplified. The reception data is acquired by performing AD conversion on the received signal by the AD conversion unit 17. The reception focus processing is performed on this reception data by the beam-former 18, the sound ray signal generated in this manner is sent to the image generation unit 21 of the diagnostic apparatus body 2, and the ultrasound image representing the tomographic image information about the tissue in the subject is generated. At this time, the signal processing unit 32 of the image generation unit 21 performs the correction of attenuation corresponding to the depth of the reflection position of the ultrasound wave and the envelope detection processing on the sound ray signal, the sound ray signal is converted into an image signal according to the method for scanning the normal television signal by the DSC 33, and various kinds of necessary image processing such as gradation processing is performed by the image processing unit 34.

In step S13, the synthesized two-dimensional image 54 corresponding to the thumbnail image 80 selected by the user, the schema image 71 on which the region of interest R selected by the user is plotted, and the ultrasound image 82 currently being captured by the ultrasound probe 1 are displayed together on the monitor 23.

In FIG. 15, a state where the thumbnail image 80 corresponding to the synthesized two-dimensional image R-CC selected by the user is surrounded by a thick line, the region of interest R in the list 81 selected by the user is surrounded by a thick line, and the synthesized two-dimensional image 54 (R-CC) corresponding to the selected thumbnail image 80, the schema image 71 superimposed and displayed on a part of the synthesized two-dimensional image 54, and the ultrasound image 82 currently being captured are displayed on the monitor 23 is shown.

Since the slice line C representing the slice plane represented by the tomosynthesis image 53 that best represents the region of interest R is drawn on the schema image 71 and the region of interest R is plotted on the slice line C, the user confirms the schema image 71. Accordingly, a scanning position of the ultrasound probe 1 can be specified, the region of interest R can be easily searched for, and the ultrasound image including the region of interest R can be generated.

In the ultrasound diagnostic apparatus according to the first embodiment, since the schema image 71 on which the region of interest R is plotted is generated based on the synthesized two-dimensional image 54, the information on the tomosynthesis image 53 accompanying the synthesized two-dimensional image 54 and best represents the region of interest R on the synthesized two-dimensional image 54, and the information on the region of interest R without storing the plurality of tomosynthesis images 53 generated by the mammography apparatus 5 in the diagnostic apparatus body 2, and an accurate diagnosis can be performed on the region of interest R of the breast without securing a large-capacity storage region in the ultrasound diagnostic apparatus.

In the above-described first embodiment, the thumbnail image 80 corresponding to the synthesized two-dimensional image R-CC is selected by the user and the schema image 71 on which the region of interest R of the synthesized two-dimensional image 54 (R-CC) corresponding to the selected thumbnail image 80 is plotted is generated. However, in a case where the region of interest R identical to the region of interest R plotted on the schema image 71 is captured on another synthesized two-dimensional image in which the imaging direction is different from the imaging direction of the synthesized two-dimensional image 54 (R-CC) and the breast of the subject is captured, for example, the synthesized two-dimensional image 54 (R-MLO), the synthesized two-dimensional image 54 (R-MLO) can also be displayed on the monitor 23.

Figure 16:
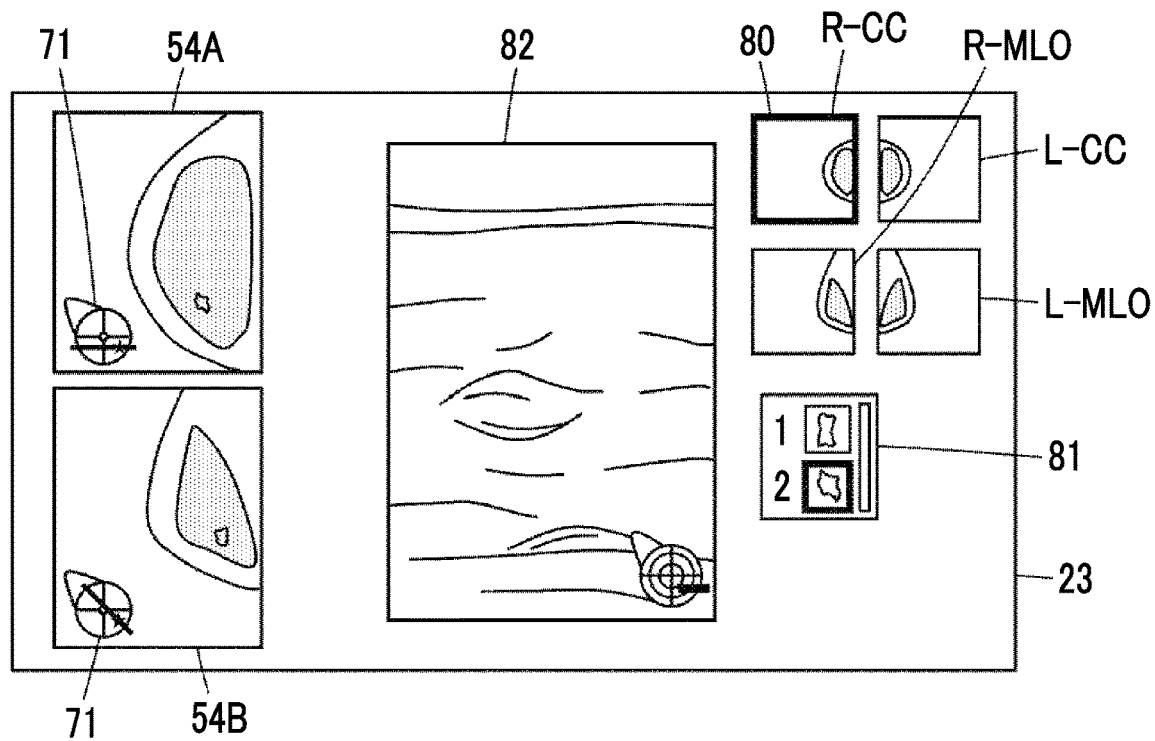
FIG. 16 is a diagram showing a display example of a monitor in an ultrasound diagnostic apparatus according to a modified example of the first embodiment.

FIG. 16 shows a state where a synthesized two-dimensional image 54A (R-CC) and a synthesized two-dimensional image 54B (R-MLO) are displayed together on the monitor 23.

For example, in a case where the region of interest R of the schema image 71 shown in FIG. 15 is designated by a double-click or the like, it is determined whether or not the identical region of interest R is captured by another synthesized two-dimensional image 54, and in a case where another synthesized two-dimensional image 54 on which the identical region of interest R is captured is present, the synthesized two-dimensional image can be displayed on the monitor 23.

For example, in the determination of whether or not the identical region of interest R is captured in the first synthesized two-dimensional image 54 and the second synthesized two-dimensional image 54 in different imaging directions, in a case where the region of interest R in the second synthesized two-dimensional image 54 is plotted on the schema image 71, the second synthesized two-dimensional image 54 is present at a close position in a threshold value with respect to the region of interest R in the first synthesized two-dimensional image 54. Since the sizes of the regions of interest R are substantially same, in a case where a difference in size is within a threshold value, it is possible to determine that the regions of interest R are identical.

In the case of so-called multiple lesions or the like, in a case where the regions of interest R having the same size are arranged at close positions and it is difficult to determine which regions of interest R are the identical regions of interest R, all the regions of interest R are preferably displayed. For example, the number X of regions of interest R that are difficult to be determined is described in the vicinity of the regions of interest R plotted on the schema image 71 to indicate that X numbers of regions of interest R are present at close positions. The X numbers of regions of interest R can be highlighted and displayed on the synthesized two-dimensional image 54.

As described above, the plurality of synthesized two-dimensional images 54 in which the imaging directions are different from each other and the identical region of interest is captured are displayed on the monitor 23, and thus, the user can more easily specify the scanning position of the ultrasound probe 1. Accordingly, it is possible to perform a more accurate diagnosis for the region of interest R of the breast. As shown in FIG. 16, even though the plurality of synthesized two-dimensional images 54A and 54B are displayed on the monitor 23, since the ultrasound image 82 currently being captured is not influenced, a line of sight of the user performing ultrasound imaging is not moved unnecessarily by the ultrasound probe 1.

In the above-described first embodiment, although the mammography apparatus 5 generates the synthesized two-dimensional image 54, the present invention is not limited thereto, and the server 6 can be configured to generate the synthesized two-dimensional image 54. In this case, the server 6 can generate the synthesized two-dimensional image 54 based on the series of radiation images acquired by tomosynthesis imaging transmitted from the mammography apparatus 5 via the network 4, or based on the plurality of reconstructed tomosynthesis images 53.

Second Embodiment

Figure 17:
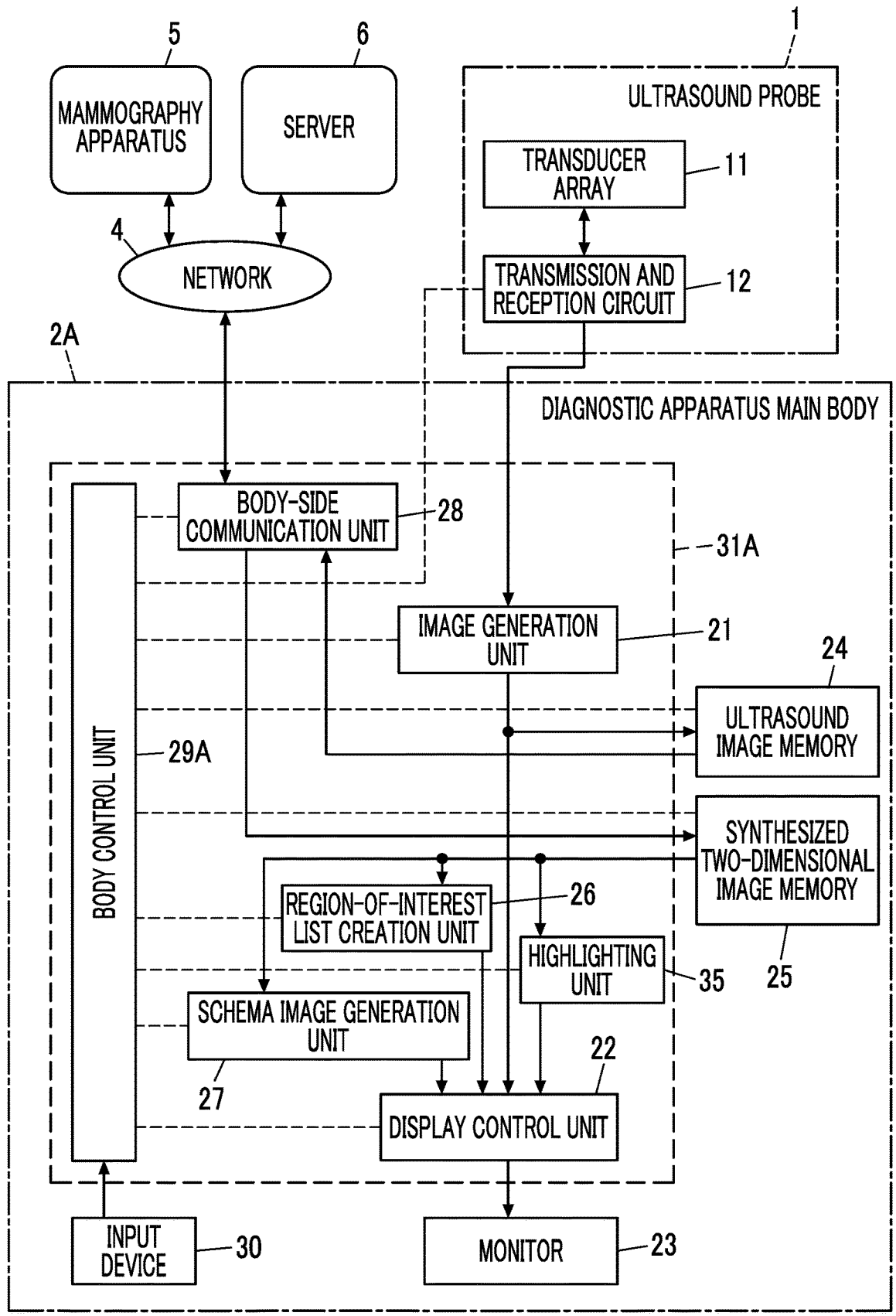
FIG. 17 is a block diagram showing a configuration of an ultrasound diagnostic apparatus according to a second embodiment.

FIG. 17 shows a configuration of a diagnostic apparatus body 2A in an ultrasound diagnostic apparatus according to a second embodiment. In the diagnostic apparatus body 2 of the ultrasound diagnostic apparatus according to the first embodiment shown in FIG. 1, in the diagnostic apparatus body 2A, since a highlighting unit 35 is newly connected between the synthesized two-dimensional image memory 25 and the display control unit 22 and a body control unit 29A is used instead of the body control unit 29, other configurations are similar to the configurations of the diagnostic apparatus body 2 according to the first embodiment.

The body control unit 29A is connected to the image generation unit 21, the display control unit 22, the ultrasound image memory 24, the synthesized two-dimensional image memory 25, the region-of-interest list creation unit 26, the schema image generation unit 27, the body-side communication unit 28, and the highlighting unit 35, and the input device 30 is connected to the body control unit 29A.

A body-side processor 31A includes the image generation unit 21, the display control unit 22, the region-of-interest list creation unit 26, the schema image generation unit 27, the body-side communication unit 28, the highlighting unit 35, and the body control unit 29A.

In a case where the region of interest R plotted on the schema image 71 is designated by the user, the highlighting unit 35 highlights a region corresponding to the region of interest R on the synthesized two-dimensional image 54 and displays the region on the monitor 23.

Figure 18:
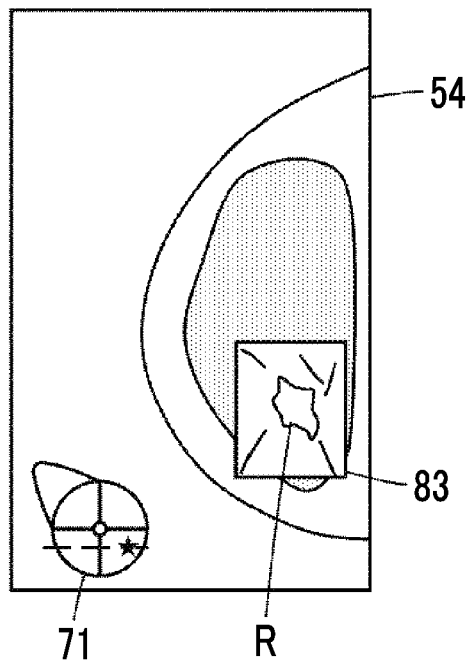
FIG. 18 is a diagram showing an example of a radiation image displayed on a monitor in the second embodiment.

For example, in a case where the region of interest R of the schema image 71 is designated by a click or the like through the input device 30, the highlighting unit 35 displays a sub-window 83 on the synthesized two-dimensional image 54 displayed on the monitor 23 as shown in FIG. 18, and the region of interest R is displayed in an enlarged manner in the sub-window 83. As described above, the region of interest R can be highlighted by the displaying in the enlarged manner.

Figure 19:
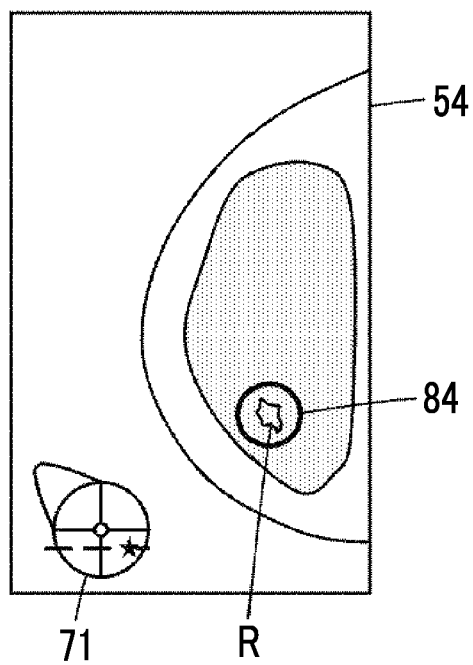
FIG. 19 is a diagram showing an example of a radiation image displayed on a monitor in a modified example of the second embodiment.

Alternatively, in a case where the region of interest R of the schema image 71 is designated, the highlighting unit 35 highlights the region of interest R by surrounding the region of interest R on the synthesized two-dimensional image 54 displayed on the monitor 23 with a highlight line 84, as shown in FIG. 19.

The highlighting unit 35 can highlight the region corresponding to the region of interest R on the synthesized two-dimensional image 54 and can display the region on the monitor 23 even for the region of interest R selected from the list 81 of regions of interest R.

By doing this, the highlighting unit 35 highlights the region of interest R on the synthesized two-dimensional image 54, and thus, the region of interest R is easily seen. Accordingly, it is possible to perform an accurate diagnosis on the region of interest R of the breast.

Third Embodiment

Figure 20:
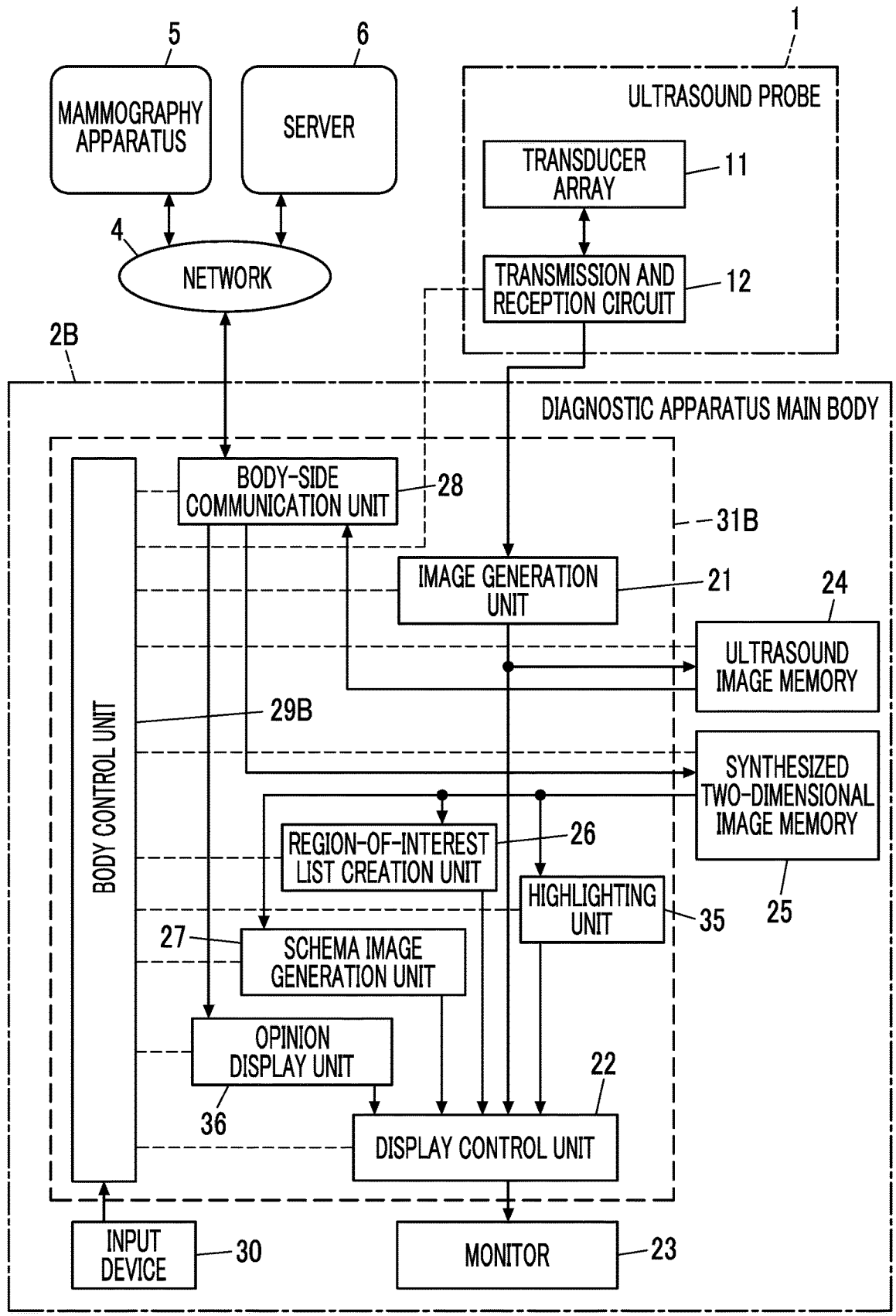
FIG. 20 is a block diagram showing a configuration of an ultrasound diagnostic apparatus according to a third embodiment.

FIG. 20 shows a configuration of a diagnostic apparatus body 2B in an ultrasound diagnostic apparatus according to a third embodiment. In the diagnostic apparatus body 2A of the ultrasound diagnostic apparatus according to the second embodiment shown in FIG. 17, in the diagnostic apparatus body 2B, since an opinion display unit 36 is newly connected to the body-side communication unit 28 and the display control unit 22 and a body control unit 29B is used instead of the body control unit 29A, other configurations are similar to the configurations of the diagnostic apparatus body 2A according to the second embodiment.

The body control unit 29B is connected to the image generation unit 21, the display control unit 22, the ultrasound image memory 24, the synthesized two-dimensional image memory 25, the region-of-interest list creation unit 26, the schema image generation unit 27, the body-side communication unit 28, the highlighting unit 35, and the opinion display unit 36, and the input device 30 is connected to the body control unit 29B.

A body-side processor 31B includes the image generation unit 21, the display control unit 22, the region-of-interest list creation unit 26, the schema image generation unit 27, the body-side communication unit 28, the highlighting unit 35, the opinion display unit 36, and the body control unit 29B.

For example, in a case where an opinion for a mammography examination is created in a reporting system (not shown) connected to the network 4, the opinion display unit 36 displays the opinion on the monitor 23.

Figure 21:
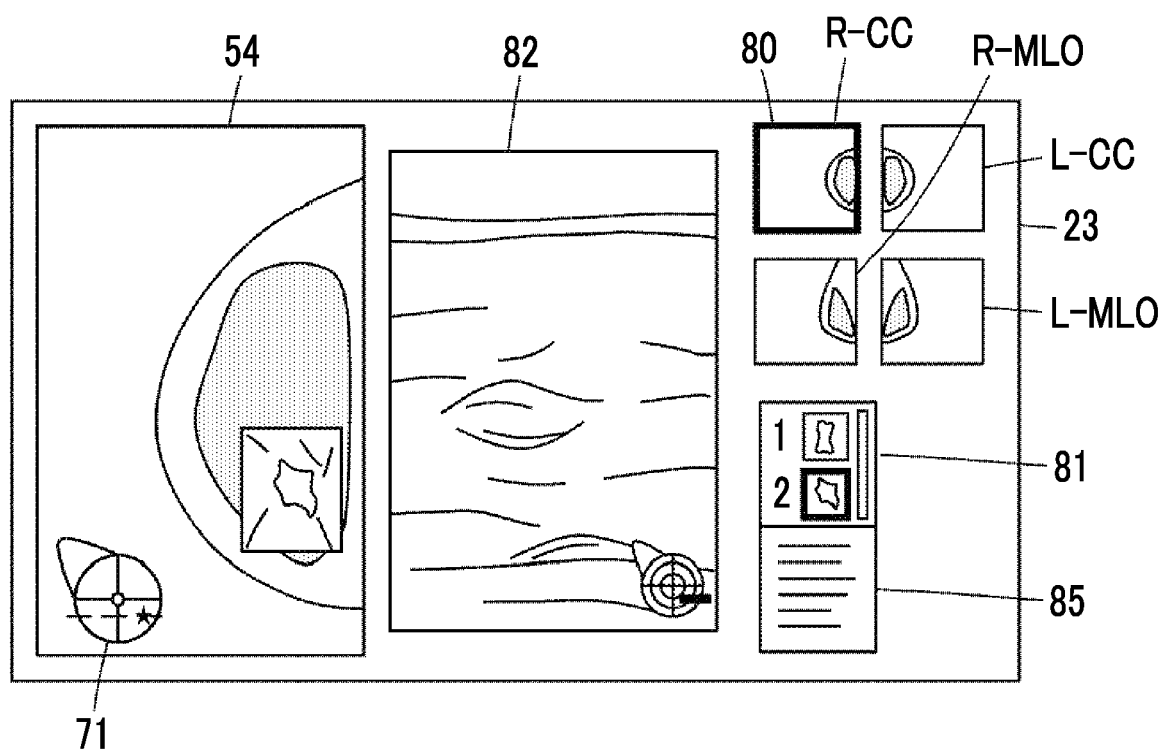
FIG. 21 is a diagram showing a display example of a monitor according to the third embodiment.

Data of the opinion created in the reporting system is received by the body-side communication unit 28 of the diagnostic apparatus body 2 via the network 4, and is sent from the body-side communication unit 28 to the opinion display unit 36. The data of the opinion is sent from the opinion display unit 36 to the display control unit 22, and as shown in FIG. 21, for example, an opinion 85 is displayed adjacent to the list 81 of regions of interest R on the monitor 23.

In a case where the opinion created in the reporting system is not only an opinion for the region of interest R but also a wide variety of opinion, the opinion display unit 36 can extract the opinion for the region of interest R from the data of the opinion acquired through the body-side communication unit 28, and can display the opinion on the monitor 23.

In a case where the opinion created in the reporting system is for a plurality of regions of interest R, the opinion display unit 36 can extract only the opinion for the region of interest R selected from the list 81 by the user, and can display the opinion on the monitor 23.

By doing this, the opinion created in the reporting system is displayed on the monitor 23, and thus, the user of the ultrasound diagnostic apparatus can perform an accurate diagnosis while more accurately recognizing the region of interest R.

Fourth Embodiment

In the above-described first embodiment, although the schema image 71 corresponding to one region of interest R selected by the user from the list 81 of regions of interest R displayed on the monitor 23 is generated, the present invention is not limited thereto. For example, in a case where any position designated by the user is included in the region of interest R on the synthesized two-dimensional image 54 displayed on the monitor 23, the schema image 71 can be generated.

Figure 22:
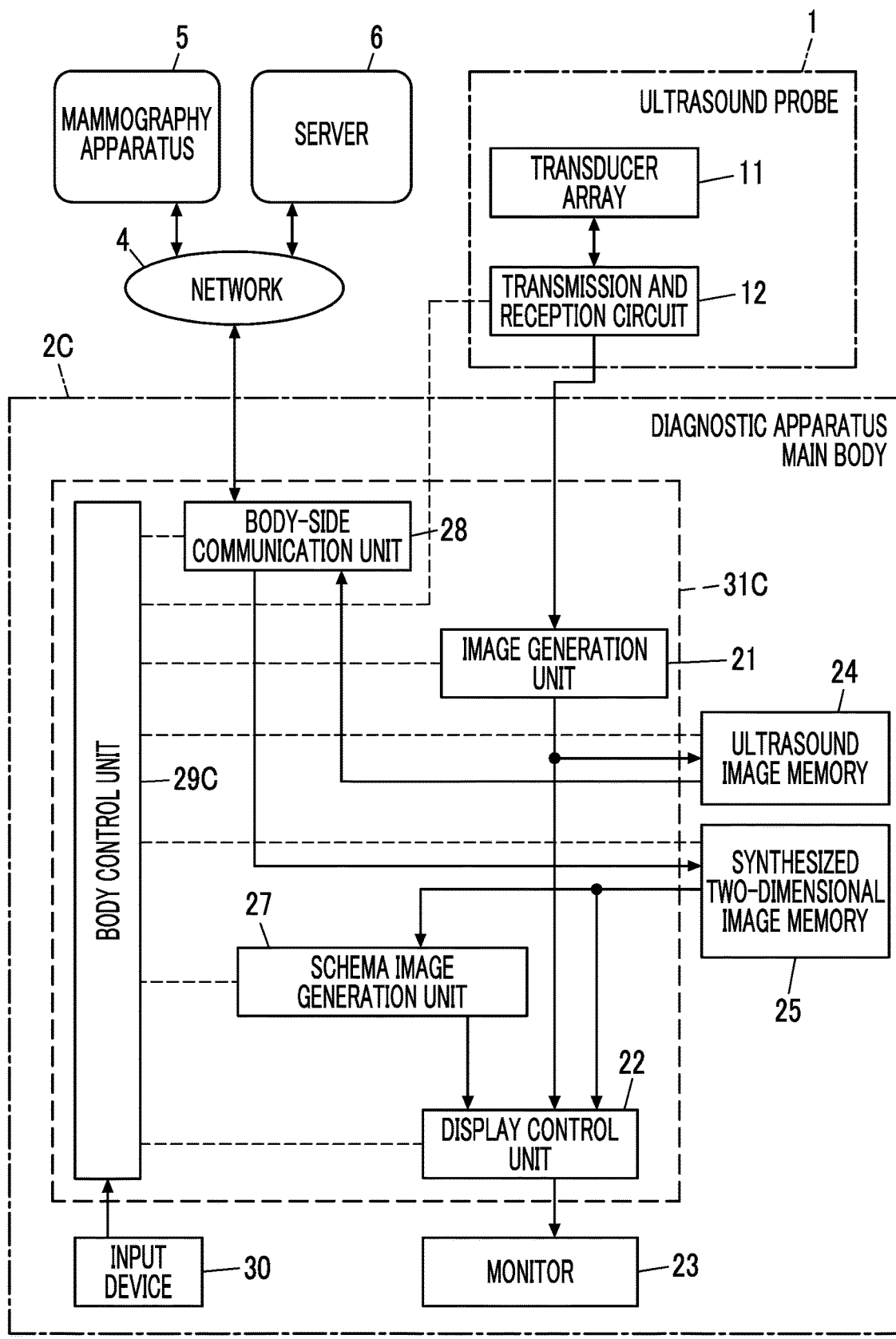
FIG. 22 is a block diagram showing a configuration of an ultrasound diagnostic apparatus according to a fourth embodiment.

FIG. 22 shows a configuration of a diagnostic apparatus body 2C in an ultrasound diagnostic apparatus according to a fourth embodiment. In the diagnostic apparatus body 2 of the ultrasound diagnostic apparatus according to the first embodiment shown in FIG. 1, in the diagnostic apparatus body 2C, since the region-of-interest list creation unit 26 is omitted and a body control unit 29C is used instead of the body control unit 29, other configurations are similar to the configurations of the diagnostic apparatus body 2 according to the first embodiment.

The body control unit 29C is connected to the image generation unit 21, the display control unit 22, the ultrasound image memory 24, the synthesized two-dimensional image memory 25, the schema image generation unit 27, and the body-side communication unit 28, and the input device 30 is connected to the body control unit 29C.

The body-side processor 31C includes the image generation unit 21, the display control unit 22, the schema image generation unit 27, the body-side communication unit 28, and the body control unit 29C.

An operation of the ultrasound diagnostic apparatus according to the fourth embodiment will be described with reference to a flowchart of FIG. 23.

Steps S5 to S7 are identical to steps S5 to S7 in the flowchart of the first embodiment shown in FIG. 14. That is, in step S5, the synthesized two-dimensional image 54 is received from the mammography apparatus 5 or the server 6 by the body-side communication unit 28 of the diagnostic apparatus body 2 via the network 4, and is stored in the synthesized two-dimensional image memory 25.

In subsequent step S6, four synthesized two-dimensional images 54 including R-CC, R-MLO, L-CC, and L-MLO received by the body control unit 29C of the diagnostic apparatus body 2, for example, the body-side communication unit 28 are displayed as the thumbnails on the monitor 23.

In step S7, the user selects one of four thumbnail images 80 corresponding to the synthesized two-dimensional images R-CC, R-MLO, L-CC, and L-MLO.

In step S7, in a case where one thumbnail image 80 is selected by the user, the processing proceeds to step S14, and the body control unit 29C displays the synthesized two-dimensional image 54 corresponding to the selected thumbnail image 80 on the monitor 23.

In step S10, the schema image generation unit 27 acquires the information about the region of interest R including the designated position by referring to the DICOM-SR or the tag of the synthesized two-dimensional image 54.

In subsequent step S15, it is determined whether or not any position on the synthesized two-dimensional image 54 displayed on the monitor 23 is designated by the user.

In step S15, in a case where it is determined that any position on the synthesized two-dimensional image 54 is designated by, for example, a click or the like through the input device 30, the processing proceeds to step S16, and it is determined whether or not the designated position is included in the region of interest R of the synthesized two-dimensional image 54.

In step S16, in a case where it is determined that the designated position is not included in the region of interest R, the processing returns to step S15, and it is determined whether or not any position on the synthesized two-dimensional image 54 is newly designated.

On the other hand, in step S16, in a case where it is determined that the designated position is included in the region of interest R, the processing proceeds to step S11, and the schema image generation unit 27 generates the schema image 71 on which the slice line C is drawn and the region of interest R is plotted on the slice line C by using the information about the region of interest R acquired in step S10.

The schema image 71 generated in this manner is displayed on the monitor 23 together with the synthesized two-dimensional image 54.

After the schema image 71 is displayed on the monitor 23, in subsequent step S12, the user captures the ultrasound image of the breast of the subject.

In step S13, the synthesized two-dimensional image 54, the schema image 71, and the ultrasound image 82 currently being captured by the ultrasound probe 1 are displayed together on the monitor 23.

As described above, even though any position is designated by the user on the synthesized two-dimensional image 54 displayed on the monitor 23 without using the list 81 of regions of interest R, similarly to the first embodiment, it is possible to perform an accurate diagnosis on the region of interest R of the breast without securing a large-capacity storage region in the ultrasound diagnostic apparatus.

In a case where there are the plurality of regions of interest R, the schema image 71 on which all the regions of interest R are plotted can be generated, and one region of interest R can be selected from among the plurality of regions of interest R plotted on the schema image 71.

In the above-described embodiments 1 to 4, although the ultrasound probe 1 and the diagnostic apparatus bodies 2, 2A, 2B, and 2C are connected in a wired manner via a cable (not shown), the present invention is not limited thereto, and the ultrasound probe 1 and the diagnostic apparatus bodies 2, 2A, 2B, and 2C can be wirelessly connected to each other.

EXPLANATION OF REFERENCES

1: ultrasound probe
2, 2A, 2B, 2C: diagnostic apparatus body
4: network
5: mammography apparatus
6: server
11: transducer array
12: transmission and reception circuit
15: pulsar
16: amplification unit
17: AD conversion unit
18: beamformer
21: image generation unit
22: display control unit
23: monitor
24: ultrasound image memory
25: synthesized two-dimensional image memory
26: region-of-interest list creation unit
27: schema image generation unit
28: body-side communication unit
29, 29A, 29B, 29C: body control unit
30: input device
31, 31A, 31B, 31C: body-side processor
32: signal processing unit
33: DSC
34: image processing unit
35: highlighting unit
36: opinion display unit
51: X-ray source
52: X-ray detector
53: tomosynthesis image
54, 54A, 54B, R-CC, R-MLO, L-CC, L-MLO: synthesized two-dimensional image
71: schema image
72: breast region
73: armpit region
80: thumbnail image
81: list
82: ultrasound image
83: sub-window
84: highlight line
85: opinion
R, R1, R2: region of interest
C, C1, C2: slice line
P0, P1: slice plane

What is claimed is:
1. An ultrasound diagnostic apparatus comprising:
an ultrasound probe;
a processor; and
a monitor, wherein the processor
    generates an ultrasound image on which a breast of a subject is captured by performing transmission and reception of an ultrasound beam by using the ultrasound probe for the subject,
    generates a schema image on which a region of interest is plotted based on
        (i) a synthesized two-dimensional image generated by using a series of radiation images obtained by tomosynthesis imaging and on which the breast of the subject is captured,
        (ii) information on a tomosynthesis image corresponding to the region of interest on the synthesized two-dimensional image, the information on the tomosynthesis image accompanying the synthesized two-dimensional image, and
        (iii) information on the region of interest; and
    displays the ultrasound image, the synthesized two-dimensional image, and the schema image on the monitor,
wherein the information on the tomosynthesis image includes a slice number and an imaging angle of the tomosynthesis image, and
wherein the processor generates the schema image including a slice line representing the tomosynthesis image and drawn at a position corresponding to the slice number with an angle as same as the imaging angle, the region of interest being plotted on the slice line.

2. The ultrasound diagnostic apparatus according to claim 1,
    wherein the processor generates the schema image on which a plurality of the regions of interest on the synthesized two-dimensional image are plotted.

3. The ultrasound diagnostic apparatus according to claim 2,
    wherein the processor creates a list of the regions of interest included in the synthesized two-dimensional image, displays the list on the monitor, and generates the schema image on which the region of interest selected from the list displayed on the monitor by a user is plotted.

4. The ultrasound diagnostic apparatus according to claim 3,
    wherein the processor highlights a region corresponding to the region of interest on the synthesized two-dimensional image and displays the region on the monitor in a case where the region of interest plotted on the schema image is designated by the user.

5. The ultrasound diagnostic apparatus according to claim 4, wherein the processor displays a sub-window on the synthesized two-dimensional image, and displays the region of interest in an enlarged manner in the sub-window.

6. The ultrasound diagnostic apparatus according to claim 4, wherein the processor surrounds the region of interest on the synthesized two-dimensional image by a highlight line.

7. The ultrasound diagnostic apparatus according to claim 2,
    wherein the processor
        displays the synthesized two-dimensional image on the monitor, and
        generates the schema image on which the region of interest is plotted in a case where any position designated by a user is included in the region of interest on the synthesized two-dimensional image displayed on the monitor.

8. The ultrasound diagnostic apparatus according to claim 1,
    wherein the processor creates a list of the regions of interest included in the synthesized two-dimensional image, displays the list on the monitor, and generates the schema image on which the region of interest selected from the list displayed on the monitor by a user is plotted.

9. The ultrasound diagnostic apparatus according to claim 8,
    wherein the processor highlights a region corresponding to the region of interest on the synthesized two-dimensional image and displays the region on the monitor in a case where the region of interest plotted on the schema image is designated by the user.

10. The ultrasound diagnostic apparatus according to claim 9, wherein the processor displays a sub-window on the synthesized two-dimensional image, and displays the region of interest in an enlarged manner in the sub-window.

11. The ultrasound diagnostic apparatus according to claim 9, wherein the processor surrounds the region of interest on the synthesized two-dimensional image by a highlight line.

12. The ultrasound diagnostic apparatus according to claim 1,
    wherein the processor
        displays the synthesized two-dimensional image on the monitor, and
        generates the schema image on which the region of interest is plotted in a case where any position designated by a user is included in the region of interest on the synthesized two-dimensional image displayed on the monitor.

13. The ultrasound diagnostic apparatus according to claim 1, further comprising:
    an opinion display unit that displays an opinion for a mammography examination together with the schema image on the monitor.

14. The ultrasound diagnostic apparatus according to claim 1, wherein the processor displays four synthesized two-dimensional images acquired by performing imaging in a cranio-caudal direction and imaging in a medio-lateral-oblique direction on each of left and right breasts of the subject as thumbnails on the monitor in addition to the ultrasound image, the synthesized two-dimensional image, and the schema image.

15. The ultrasound diagnostic apparatus according to claim 1, wherein, in a case where a region of interest corresponding to the region of interest plotted on the schema image is imaged on another synthesized two-dimensional image generated by using another series of radiation images in which the breast of the subject is imaged by tomosynthesis imaging with another imaging direction different from an imaging direction of tomosynthesis imaging for obtaining the series of radiation images used for the generation of the synthesized two-dimensional image, the processor displays the synthesized two-dimensional image and the other synthesized two-dimensional image together with the ultrasound image and the schema image on the monitor.

16. The ultrasound diagnostic apparatus according to claim 1, wherein the processor stores identification information of the region of interest, a position of the region of interest, a slice number of the tomosynthesis image corresponding to the region of interest, and an imaging angle in a file that does not include a tag or an image accompanying the synthesized two-dimensional image.

17. The ultrasound diagnostic apparatus according to claim 1, further comprising:
   a memory that stores the synthesized two-dimensional image.

18. A control method of an ultrasound diagnostic apparatus, comprising:
   generating an ultrasound image on which a breast of a subject is captured by performing transmission and reception of an ultrasound beam by using an ultrasound probe for the subject;
   generating a schema image on which a region of interest is plotted based on
      (i) a synthesized two-dimensional image generated by using a series of radiation images obtained by tomosynthesis imaging and on which the breast of the subject is captured,
      (ii) information on a tomosynthesis image corresponding to the region of interest on the synthesized two-dimensional image, the information on the tomosynthesis image accompanying the synthesized two-dimensional image, and
      (iii) information on the region of interest; and
   displaying the ultrasound image, the synthesized two-dimensional image, and the schema image on a monitor,
   wherein the information on the tomosynthesis image includes a slice number and an imaging angle of the tomosynthesis image, and
   wherein the schema image includes a slice line representing the tomosynthesis image and drawn at a position corresponding to the slice number with an angle as same as the imaging angle, the region of interest being plotted on the slice line.

* * * * *